(12) United States Patent
Eguchi et al.

(10) Patent No.: US 8,691,261 B2
(45) Date of Patent: Apr. 8, 2014

(54) DRUG, DRUG GUIDANCE SYSTEM, MAGNETIC DETECTION SYSTEM, AND DRUG DESIGN METHOD

(75) Inventors: Haruki Eguchi, Tokyo (JP); Yoshihiro Ishikawa, Tokyo (JP)

(73) Assignees: IHI Corporation (JP); Yoshihiro Ishikawa (JP)

(*) Notice: Subject to any disclaimer, the term of this patent is extended or adjusted under 35 U.S.C. 154(b) by 0 days.

(21) Appl. No.: 13/552,343

(22) Filed: Jul. 18, 2012

(65) Prior Publication Data

US 2012/0283505 A1 Nov. 8, 2012

Related U.S. Application Data

(60) Division of application No. 12/306,706, filed as application No. PCT/JP2007/063011 on Jun. 28, 2007, now Pat. No. 8,246,975, which is a continuation-in-part of application No. 12/063,768, filed as application No. PCT/JP2006/317027 on Aug. 23, 2006, now abandoned.

(30) Foreign Application Priority Data

| Aug. 31, 2005 | (JP) | 2005-251190 |
| Jun. 28, 2006 | (JP) | 2006-177971 |
| Mar. 7, 2007 | (JP) | 2007-056624 |

(51) Int. Cl.

| A61F 2/00 | (2006.01) |
| A61K 9/16 | (2006.01) |
| A61K 9/50 | (2006.01) |
| A61B 17/52 | (2006.01) |
| A61B 5/00 | (2006.01) |
| A61N 2/00 | (2006.01) |
| G06F 9/44 | (2006.01) |
| G06F 13/12 | (2006.01) |
| G06F 19/16 | (2011.01) |
| G06G 7/48 | (2006.01) |

(52) U.S. Cl.
USPC ............ 424/423; 424/491; 424/499; 600/9; 600/12; 600/409; 702/22; 702/27; 702/82; 702/115; 703/6; 703/11; 703/12; 703/21

(58) Field of Classification Search
USPC ................ 703/12, 6, 11, 21; 600/9, 12, 409; 702/22, 27, 82, 115; 424/423, 491, 499
See application file for complete search history.

(56) References Cited

U.S. PATENT DOCUMENTS

| 4,727,068 A | 2/1988 | Abrams et al. |
| 4,871,716 A | 10/1989 | Longo et al. ............... 424/9.322 |
| 5,549,915 A * | 8/1996 | Volkonsky et al. ........... 424/490 |
| 6,162,469 A | 12/2000 | Atarashi et al. |
| 2007/0092549 A1 | 4/2007 | Tuszynski et al. ............ 424/423 |
| 2009/0169484 A1 | 7/2009 | Eguchi et al. |

FOREIGN PATENT DOCUMENTS

| CA | 2113245 | 7/1994 |
| EP | 0 800 829 | 10/1997 |

(Continued)

OTHER PUBLICATIONS

Extended European Search Report, dated Jun. 16, 2011 issued in corresponding European Application No. EP 10006344.5, total 3 pages.

(Continued)

Primary Examiner — Jane C Oswecki
(74) Attorney, Agent, or Firm — Ostrolenk Faber LLP

(57) ABSTRACT

It is intended to provide a drug delivery system which makes it possible to solve the existing technical problems and is easily usable in practice. A drug, which comprises an organic compound or an inorganic compound and has been magnetized by modifying a side chain and/or crosslinking side chains, is induced by a magnetic force into target tissues or an affected part.

31 Claims, 23 Drawing Sheets

(56) References Cited

FOREIGN PATENT DOCUMENTS

| EP | 1 097 711 | 5/2001 | | |
|---|---|---|---|---|
| JP | 49-13316 | 2/1974 | | |
| JP | 49-13317 | 2/1974 | | |
| JP | 62-174014 | 7/1987 | | |
| JP | 62-192383 | 8/1987 | | |
| JP | 3-21319 | 1/1991 | | |
| JP | 5-45932 | 2/1993 | | |
| JP | 5-23276 | 4/1993 | | |
| JP | 5-216967 | 8/1993 | | |
| JP | 05-216967 | * 8/1993 | ............ | G06F 15/60 |
| JP | 7-149799 | 6/1995 | | |
| JP | 07267857 | 10/1995 | | |
| JP | 07-296045 | * 11/1995 | ............ | G06F 17/50 |
| JP | 7-296045 | 11/1995 | | |
| JP | 8-506111 | 7/1996 | | |
| JP | 9-328438 | 12/1997 | | |
| JP | 09-329602 | 12/1997 | | |
| JP | 10-310796 | 11/1998 | | |
| JP | 11-006825 | 1/1999 | | |
| JP | 11-507646 | 7/1999 | | |
| JP | 11-217385 | 8/1999 | | |
| JP | 2000-269013 | 9/2000 | | |
| JP | 2001-010978 | 1/2001 | | |
| JP | 2002-093606 | 3/2002 | | |
| JP | 2004-514724 | 5/2004 | | |
| JP | 2004-239685 | 8/2004 | | |
| JP | 2005-154402 | 6/2005 | | |
| JP | 2005-522495 | 7/2005 | | |
| JP | 2006-528506 | 12/2006 | | |
| JP | 2007-091710 | 4/2007 | | |
| JP | 2008-115129 | 5/2008 | | |
| JP | 2008-117969 | 5/2008 | | |
| JP | 2009-173631 | 8/2009 | | |
| RU | 2255734 | 7/2005 | | |
| WO | 94-16683 | 8/1994 | | |
| WO | 96/40149 | 12/1996 | | |
| WO | WO 99/64004 | 12/1999 | | |
| WO | 02/44187 | 6/2002 | | |
| WO | 03/086563 | 10/2003 | | |
| WO | 2005/0011810 | 2/2005 | | |
| WO | WO 2007/026725 | 3/2007 | | |

OTHER PUBLICATIONS

Sylvain Routier, et al., "DNA Cleavage by Hydroxy—Salicylidene—Ethylendiamine—Iron Complexes" Nucleic Acids Research, 1999 Oxford University Press, Vol. 27, No. 21. Total 7 pages.

International Search Report and Written Opinion in English dated Jun. 11, 2007, issued in corresponding PCT Application No. PCT/JP2006/317027 filed Aug. 23, 2006.

Zhang Y, et al., *Surface modification of superparamagnetic magnetite nanoparticles and their intracellular uptake*, Biomaterials, Elsevier Science Publishers BV., Barking, GB, pp. 1553-1561, vol. 23 (7), (Apr. 2002).

Gupta A, et al., *Receptor-Mediated targeting of magnetic nanoparticles using insulin as a surface ligand to prevent endocytosis*, IEE Transactions on Nanobioscience, pp. 255-261, vol. 2 (4), (Dec. 2003).

Sestier C, et al., *Surface modification of superparamagnetic nanoparticles(Ferrofluid) studied with particle electrophesis: Application to the specific targeting of cells*, pp. 1220-1226, vol. 19 (7), (Jun. 1998).

Torchilin V P, et al., *Magnetic Sephadex as a carrier for enzyme immobilization and drug targeting*, Journal of Biomedical Materials Research, pp. 461-466, vol. 19 (4), (Apr. 1985).

Bhat S V. et al., *Structures and stereochemistry of new labdane diterpenoids from coleus-forskohlii*, Tetrahedron Letters, pp. 1669-1672, vol. 18 (19), (1977).

Leclaire, et al., *A simple access to a forskolin precursor*, Tetrahedron Letters, pp. 6331-6334, vol. 30 (46), (1989).

Rotella, et al., *N-3-Substituted Imidazoquinazolinones: Potent and Selective PDE5 Inhibitors as Potential Agents for Treatment of Erectile Dysfunction*, J. Med. Chem., American Chemical Society, pp. 1257-1263, vol. 43 (7), (Apr. 2000).

Rotella, et al.,*Optimization of Substituted N-3-Benzylimidazoquinazolinone Sulfonamides as Potent and Selective PDE5 Inhibitors*, J. Med. Chem., American Chemical Society, pp. 5037-5043, vol. 43 (26), (Dec. 2000).

Leopold, et al., *Carcinogenicity of Antitumor cis-Platinum(II) Coordination Complexes in the Mouse and Rat*, Cancer Research, pp. 913-918, vol. 39(3), (Mar. 1979).

Takahashi, et al., *Heat enhances the cytotoxicity of cis-diamminedichloroplatinum (II) and its analogues cis-1,1-cyclobutanedicarboxylato(2R)-2-methyl-1,4-butanediammineplatinum(II) and cis-diammine(glycolato)platinum in vitro*, Cancer Chemotherapy and Pharmacology, pp. 31-35, vol. 33 (1), (Jan. 1994).

Mombru, et al., *Multilevel ferromagnetic behavior of room-temperature bulk magnetic graphite*, Physical Review B, Concensed Matter and Materials Physics, American Institute of Physics, pp. 100404-1, vol. 71 (10), (Mar. 2005).

Halbreich, et al., *Biomedical applications of maghemite ferrofluid*, Biochimie, Masson, pp. 379-390, vol. 80 (5/6), (1998).

Gupta, et al. *Magnetically Controlled Targeted Micro-Carrier Systems*, Life Sciences, Pergamon Press, pp. 175-186, vol. 44 (3), (1989).

Alexiou, et al., *Lorcoregional Cancer Treatment with Magnetic Drug Targeting*, Cancer Research, American Assoc. for Cancer Research, pp. 6641-6648, vol. 60 (23), (Dec. 2000).

Pardo, et al., *Synthesis and characterization of stable room temperature bulk ferromagnetic graphite*, Carbon, Elsevier, pp. 565-569, vol. 44 (3), (Sep. 2005).

Ibrahim et al., *New magnetic drug carrier*, The Journal of Pharmacy and Pharmacology, pp. 59-61, vol. 35 (1), (Jan. 1983).

Kortus, J. *Electronic structure, magnetic ordering and phonons in molecules and solids*, Internet Article [online] ( pp. 1-146): http://deposit.ddb.de/cgi-bin/dokserv?idn=969764359.pdf [retrieved on Oct. 16, 20071].

Leopold et al., Cancer Research, 39:913-918 (1979).

Siegfried Drewes et al., "Recent findings on natural products with erectile-dysfunction activity"; (2003); Phytochemistry (Pergamon/Elsevier; www.sciencedirect.com); 62:1019-1025.

Lewis et al., (Journal of the Chemical Society [Section] A: Inorganic, Physical & Theoretical, 1967, No. 7, pp. 1014-1018).

Alexiou et al., "Magnetic mitoxantrone nanoparticle detection by histology, X-ray and MRI after magnetic tumor targeting", Journal of Magnetism and Magnetic Materials, 2001, 225:187-193.

Fortin-Ripoche et al., "Magnetic Targeting of Magnetoliposomes to Solid Tumors with MR Imaging Monitoring in Mice: Feasibility", Radiology, May 2006, 239(2):415-424.

Hafeli et al, "Effective Targeting of Magnetic Radioactive Y-microspheres to Tumor Cells by an Externally Applied Magnetic Field. Preliminary in Vitro and in Vivo Results", Nucl. Med. Biol., 1995, 22(2):147-155.

Srihari et al. "Reactions of Fluorenylidene Nitrile Ylides with (Salen) metal Complexes", Inorg. Chem. 1990, 29:3154-3157.

C. Alexiou et al., "Magnetic mitoxantrone nanoparticle detection by histology, X-ray and MRI after magnetic tumor targeting", *Journal of Magnetism and Magnetic Materials*, 225:187-193 (2001).

J. Fortin-Ripoche et al., "Magnetic Targeting of Magnetoliposomes to Solid Tumors with MR Imaging Monitoring in Mice: Feasibility", Radiology, 239(2):415-424 (2006).

U. Hafeli et al., "Effective Targeting of Magnetic Radioactive $^{90}$Y-microspheres to Tumor Cells by an Externally Applies Magnetic Filed. Preliminary In Vitro and In Vivo Results", *Nucl. Med, Biol.*, 22(2):147-155 (1995).

J. Lewis et al., "The Preparation and Magnetic Properties of Some Oxy-bridged Binuclear Iron (III) Schiff-base Complexes", *J. Chem. Soc. (A)*, pp. 1014-1018 (1967).

S. SriHari et al., "Reactions of Fluorenylidene Nitrile Ylides with (Salen)metal Complexes", *Inorg. Chem.*, 29:3154-3157 (1990).

* cited by examiner

FIG.11

| COMPOUND NAME | RELATIVE SPIN-CHARGE DENSITY |
|---|---|
| MAGNETITE ($Fe_3O_4$) PARTICLE | 1 |
| NK121 | 0.608 |
| Cis-Pt-a3 | 0.186 |
| Cis-Pt-b2 | 0.128 |
| Cis-Pt-f2 | 0.162 |
| Cis-Pt-n3 | 0.141 |
| Cis-Pd-a3 | 0.197 |
| Cis-Pd-b2 | 0.165 |
| Cis-Pd-f2 | 0.207 |
| Cis-Pd-g1 | 0.108 |
| Cis-Pd-n3 | 0.163 |
| Cis-Pd-o3 | 0.173 |
| Cis-Rh-a3 | 0.492 |
| Cis-Rh-n3 | 0.0886 |
| Cis-Rh-o3 | 0.229 |
| Cis-Ir-NK121 | 0.0709 |
| Cis-Ir-a3 | 0.0438 |
| Cis-Ir-n3 | 0.0506 |
| Cis-Ir-o3 | 0.0579 |
| Cis-Au-a3 | 0.145 |
| Cis-Ni-NK121 | 0.407 |

| COMPOUND NAME | RELATIVE SPIN-CHARGE DENSITY |
|---|---|
| Cis-Ni-a3 | 0.277 |
| Cis-Ni-b2 | 0.302 |
| Cis-Ni-c1 | 0.532 |
| Cis-Ni-d1 | 0.539 |
| Cis-Ni-e1 | 0.336 |
| Cis-Ni-f2 | 0.477 |
| Cis-Ni-g1 | 0.568 |
| Cis-Ni-n3 | 0.489 |
| Cis-Ni-o3 | 0.401 |
| Cis-Ag-a3 | 0.249 |
| Cis-Cu-a3 | 0.204 |
| Cis-Cu-o3 | 0.116 |
| Cis-Co-NK121 | 0.423 |
| Cis-Co-a3 | 0.942 |
| Cis-Co-b2 | 0.695 |
| Cis-Co-c2 | 0.949 |
| Cis-Co-d1 | 0.866 |
| Cis-Co-e1 | 0.633 |
| Cis-Co-f2 | 0.826 |
| Cis-Co-g1 | 0.715 |
| Cis-Co-n3 | 0.350 |
| Cis-Co-o3 | 0.318 |

FIG.13

REACTION 1 : cis−[PtCl$_2$(NH$_3$)$_2$] + H$_2$O → cis−[PtCl(OH$_2$)(NH$_3$)$_2$]$^+$ + Cl$^-$ REACTION 2 : cis−[PtCl(OH$_2$)(NH$_3$)$_2$]$^+$ + H$_2$O → cis−[Pt(OH$_2$)$_2$(NH$_3$)$_2$]$^{2+}$ + Cl$^-$ REACTION 3 : [PtCl(dien)]$^+$ + H$_2$O → [Pt(OH$_2$)$_2$(dien)]$^{2+}$ + Cl$^-$ dien = (NH$_2$CH$_2$CH$_2$)$_2$NH FIG.19
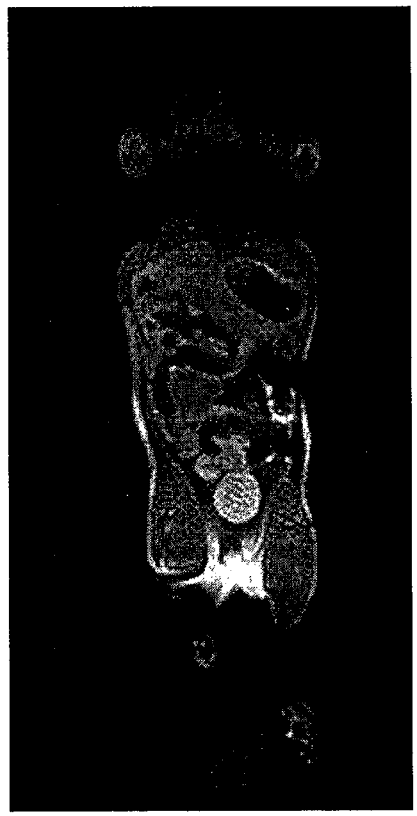
BEFORE ADMINISTRATION
AFTER ADMINISTRATION n=4, P<0.05

DRUG, DRUG GUIDANCE SYSTEM, MAGNETIC DETECTION SYSTEM, AND DRUG DESIGN METHOD

CROSS REFERENCE TO RELATED APPLICATIONS

The present application is a divisional of U.S. patent application Ser. No. 12/306,706, filed Jul. 20, 2009 now U.S. Pat. No. 8,246,975, which is a U.S.C. §371 National Phase conversion of PCT/JP2007/063011, filed Jun. 28, 2007, which claims benefit of Japanese Application No. 2006-177971, filed Jun. 28, 2006 and Japanese Application No. 2007-056624, filed Mar. 7, 2007, the contents of which are incorporated in full herein by reference. The PCT International Application was published in the Japanese language.

The present application is also a continuation-in-part of U.S. patent application Ser. No. 12/063,768, filed Feb. 14, 2008 now abandoned, which is a U.S.C. §371 National Phase conversion of PCT/JP2006/317027, filed Aug. 23, 2006, which claims benefit of Japanese Application No. 2005-251190, filed Aug. 31, 2005 and Japanese Application No. 2006-177971, filed Jun. 28, 2006, the contents of which are incorporated in full herein by reference. The PCT International Application was published in the Japanese language.

FIELD OF THE INVENTION

The present invention relates to a drug, a drug guidance system, a magnetic detection system, and a drug design method.

BACKGROUND

Generally, drugs administered to the living body reach target sites and cause therapeutic effects by exerting pharmacological effects at the localized target sites. However, there will not be a cure if drugs reach tissues other than the target sites (that is, normal tissues). Consequently, how to guide drugs to the target sites efficiently is important in terms of therapeutic strategy. Such a technology for guiding drugs to the target sites is called drug delivery and research and development thereof have been actively carried out in recent years. These drug delivery methods have at least two merits. One is that a sufficiently high drug concentration is obtained in affected tissues. This is advantageous because pharmacological effects are achieved only when the drug concentration in the target site is higher than a certain value, and therapeutic effects can not be expected when the concentration is low. Second is that the drug delivery methods guide drugs to affected tissues only and do not guide drugs to normal tissues unnecessarily. Side effects can thereby be suppressed.

Such drug delivery methods exert their effects most in cancer treatments using anticancer agents. Since most anticancer agents suppress cell growth of cancer cells which are actively dividing, they also suppress cell growth in normal tissues where cells are actively dividing such as, for example, bone marrow, hair-roots, or gastrointestinal mucosa. On this account, side effects such as anemia, hair loss, and vomiting appear in cancer patients who have received administration of anticancer agents. Dosage has to be restricted since these side effects would be heavy burdens on patients and thus, there is a problem in that pharmacological effects of anticancer agents cannot be obtained sufficiently. Furthermore, there is a concern of patients dying due to the side effects in worst cases. Accordingly, it is hoped that cancer treatments can be carried out efficiently while suppressing the side effects by guiding the anticancer agents until they reach cancer cells with drug delivery methods and allowing the agents to exert their pharmacological effects on cancer cells, specifically.

Apart from anticancer agents, for example, application of the drug delivery methods to agents for treating male erectile dysfunction is considered. There are examples of significant systemic hypotension resulting in deaths caused by the use of agents for treating male erectile dysfunction when combined with nitro preparations and thus, it is a problem particularly for males of middle and old age with heart disease. This is because the agents for treating erectile dysfunction do not necessarily concentrate at the target site, act on systemic blood vessels, and thereby increase vasodilation effects of nitro preparations. Accordingly, it is considered that the side effects resulting from the combined use with nitro preparations can be suppressed by guiding the agents for treating male erectile dysfunction until they reach the target site with drug delivery methods and allowing the agents to exert their pharmacological effects on the target site specifically.

As a specific method of drug delivery methods, for example, guidance to the target site using supports (carriers) is being studied and this method is to load drugs onto supports that tend to concentrate in the target site and thereby make the supports transport the drugs to the target site. As supports, use of various types of antibodies, microspheres, or magnetic bodies has been discussed. Among them, magnetic bodies are those that are regarded as particularly hopeful and a method to attach the supports, which are magnetic bodies, to the drugs and make them accumulate in the target site by means of a magnetic field has been examined (for example, refer to the following Patent Document 1). Since this guiding method is easy and simple and makes treatment which targets the target site possible, it is considered to be an effective method especially for anticancer agents with high cytotoxicity.

Patent Document 1: Japanese Laid-Open Patent Application No. 2001-10978

BRIEF SUMMARY OF THE INVENTION

However, when the supports, which are magnetic bodies, are used as carriers as described above, difficulties in oral administration, the large size of carrier molecules in general, or technical problems in bond strength and affinity with the drug molecules have been pointed out and thus, practical application has been difficult.

The present invention addresses the abovementioned problems, with an object of realizing a drug delivery system which is capable of solving conventional technical problems and which is easy to put into practical application.

In order to achieve the above object according to a first aspect of the present invention relating to a drug, the drug is composed of an organic or inorganic compound, and is made magnetic by modification of side chains and/or crosslinking between side chains.

According to a second aspect of the present invention relating to a drug, the organic compound in the first aspect is forskolin.

Moreover, as a third aspect of the present invention relating to a drug according to the first aspect, the organic compound is a composition effective in the treatment of male erectile dysfunction.

Moreover, as a fourth aspect of the present invention relating to a drug according to the first aspect, the inorganic compound is a metal complex.

Moreover, as a fifth aspect of the present invention relating to a drug according to the fourth aspect, the metal complex is a cis geometric isomer with anticancer properties.

Moreover, as a sixth aspect of the present invention relating to a drug according to the fifth aspect, the cis geometric isomer is cisplatin.

Moreover, as a first aspect of the present invention relating to a drug guidance system, a drug of any one of the above first to sixth aspects administered to a body is guided to a predetermined target site using the magnetism of the drug.

Moreover, as a first aspect of the present invention relating to a magnetic detection system, by detecting magnetism of a drug of any one of the above first to sixth aspects administered in a body, the dynamics of the drug are detected.

Moreover, as a first aspect of the present invention relating to a drug design method, a molecular model having modified side chains and/or crosslinked side chains is set with respect to an organic or inorganic compound used as a drug; whether or not the molecular model is magnetic is determined from a spin-charge density distribution obtained by a numerical calculation for the molecular model; and then the drug is designed based on the molecular model that has been determined to be magnetic.

Moreover, as a second aspect of the present invention relating to a drug design method according to the first aspect, whether the molecular model is ferromagnetic or ferrimagnetic is determined based on the spin-charge density distribution.

Moreover, as a third aspect of the present invention relating to a drug design method according to in the first aspect, the magnetic strength of the molecular model is determined based on the spin-charge density distribution.

According to the present invention, since drugs themselves will be magnetic, it is possible to guide the drugs to the target sites in the body by use of magnetism of the drugs themselves without using supports made from magnetic bodies as in the conventional cases. As a result, conventional problems such as difficulties in oral administration, the large size of carrier molecules in general, or technical problems in bond strength and affinity with the drug molecules can be resolved. Furthermore, it is possible to realize a drug delivery system which is easy to put into practical application.

BRIEF DESCRIPTION OF THE DRAWINGS

FIG. 11 is an analytical result of spin-charge densities of a cisplatin derivative and a derivative derived by the substitution of platinum of the cisplatin derivative into another metal element in one embodiment of the present invention.

FIG. 13 is a diagram showing a hydrolysis process of cisplatin in a living body in one embodiment of the present invention.

FIG. 19 shows MRI output images of an example in which a magnetic drug is administered to a rat.

DESCRIPTION OF REFERENCE SYMBOLS

A, B: forskolin derivatives

DETAILED DESCRIPTION OF THE INVENTION

Hereunder is a description of one embodiment of the present invention, with reference to the drawings.

First Embodiment

Firstly, the first embodiment is described using an organic compound, more specifically, forskolin, as a drug candidate agent.

Figure 1:
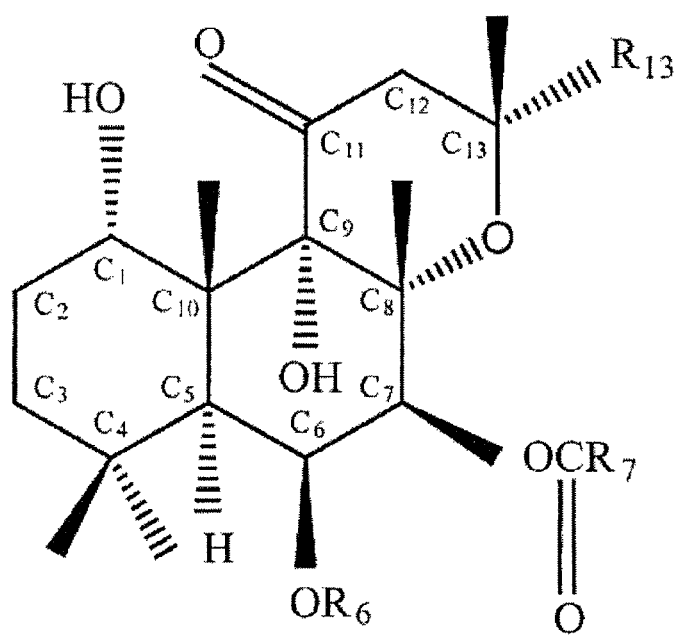
FIG. 1 is a diagram of a basic molecular structural model of forskolin in one embodiment of the present invention.

FIG. 1 is a diagram showing a basic molecular structural model of forskolin. In this drawing, $R_6$, $R_7$, and $R_{13}$ show positions bonded with an atom or a molecule for modifying a side chain of forskolin. Depending on the type of atom or molecule bonded to these positions, the physical property of forskolin varies. In this drawing, one having H bonded to $R_6$, $CH_3$ bonded to $R_7$, and $CH=CH_2$ bonded to $R_{13}$ is naturally occurring forskolin, and one having the side chain structure changed artificially, that is, forskolin produced by changing the atom or molecule for modifying $R_6$, $R_7$, and $R_{13}$, is called a forskolin derivative. In FIG. 1, $C_1$ to $C_{13}$ represent a carbon atom (C).

Figure 2:
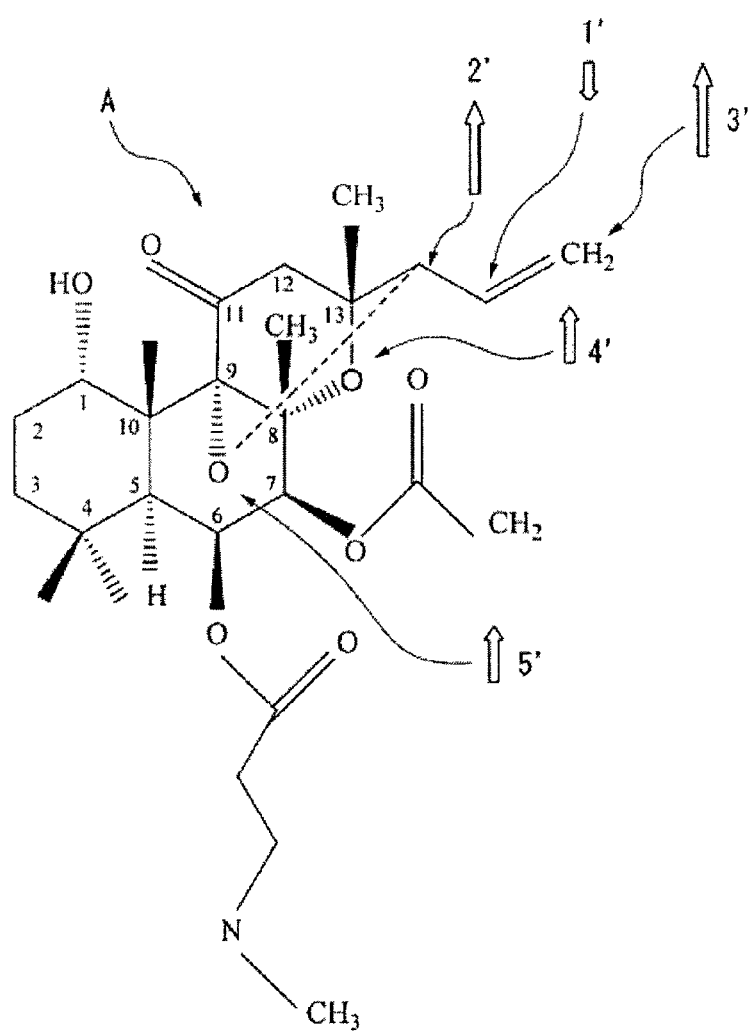
FIG. 2 is a diagram of a molecular structural model of a ferrimagnetic forskolin derivative A in one embodiment of the present invention.

FIG. 2 is a diagram showing a basic molecular structural model of a magnetic (ferrimagnetic) forskolin derivative A. As shown in this drawing, the forskolin derivative A is one where $R_6$ of the abovementioned naturally occurring forskolin is changed into $COCH_2CH_2NCH_3$, $R_7$ is changed to $CH_3$, and the oxygen atom (O) bonded to $C_9$ and the carbon atom bonded to $C_{13}$ are crosslinked.

Figure 3:
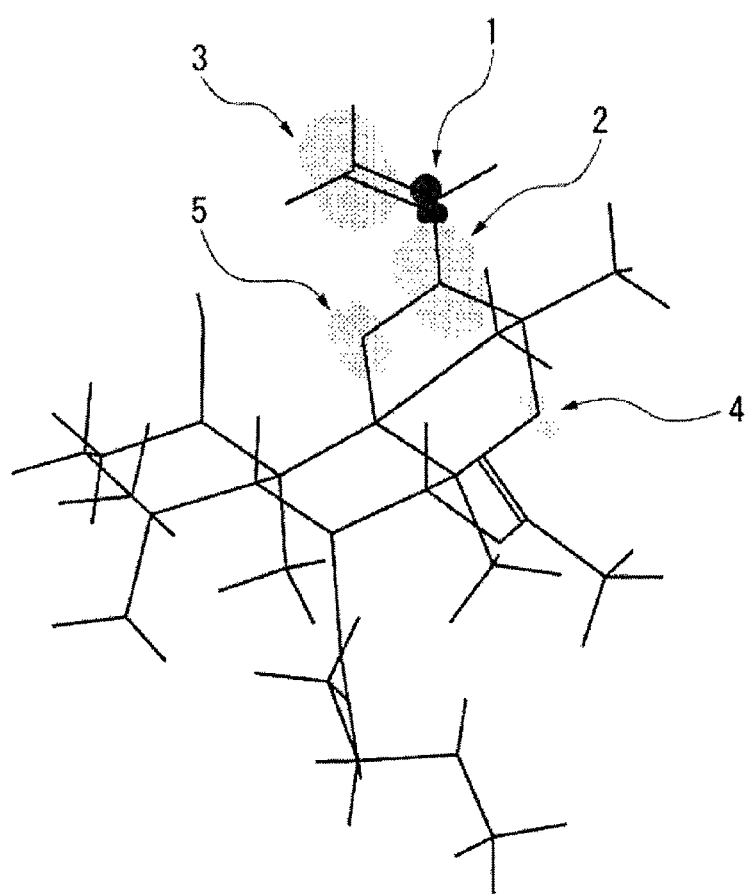
FIG. 3 is a diagram showing a three-dimensional molecular structural model of the forskolin derivative A and its spin-charge density distribution, in one embodiment of the present invention.

FIG. 3 shows a three-dimensional molecular structure of the forskolin derivative A ad its spin-charge density distribution obtained by a computer simulation based on a well-known first principle molecular dynamics method. The first principle molecular dynamics method is disclosed in Delley, B. J. Chem. Phys., 1990, 92, 508-517, Delley, B. J. Chem. Phys., 2000, 113, 7756-7764, Haselgrove, C. B. Math Comp., 1961, 15, 323-337, Ellis, D. E. Int. J. Quantum Chem., 1968, 2S, 35-42, Ellis, D. E.; Painter, G. S. Phys. Rev. B, 1970, 2, 2887-2898.

In FIG. 3, region 1 shows a downward spin-charge density, and regions 2 to 5 show upward spin-charge densities. These regions are selected because, as a result of calculation of a contour line of the spin-charge densities, these region show high spin-charge densities. The property of magnetism of a compound is decided by balance between upward spin and downward spin. Therefore, as shown in FIG. 2, since a downward spin state 1' and upward spin states 2' to 5' are mixed in the forskolin derivative A, it is found to be a ferrimagnetic body.

Figure 4:
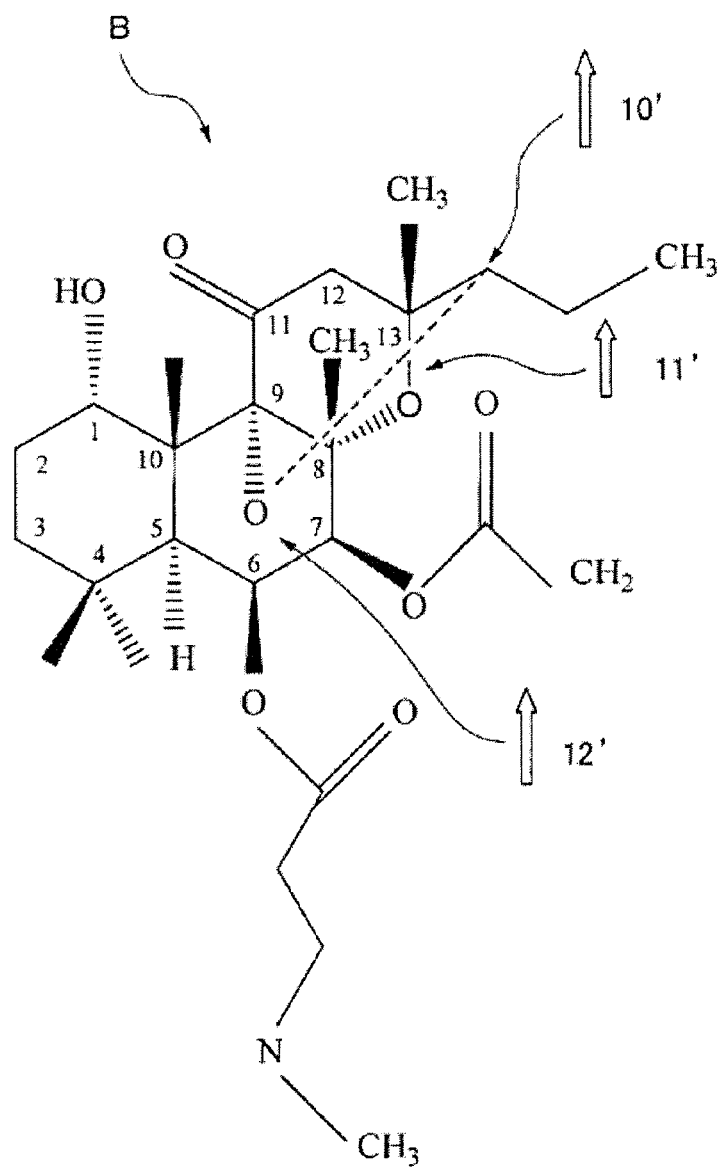
FIG. 4 is a diagram of a molecular structural model of a ferromagnetic forskolin derivative B in one embodiment of the present invention.

On the other hand, FIG. 4 is a diagram showing a basic molecular structural model of a magnetic (ferromagnetic) forskolin derivative B. As shown in this drawing, the forskolin derivative B is one where $R_6$ of the abovementioned naturally occurring forskolin is changed into $COCH_2CH_2NCH_3$, $R_7$ is $CH_3$, $R_{13}$ is changed into $CH-CH_2-CH_3$, and the oxygen atom bonded to $C_9$ and the carbon atom bonded to $C_{13}$ are crosslinked.

Figure 5:
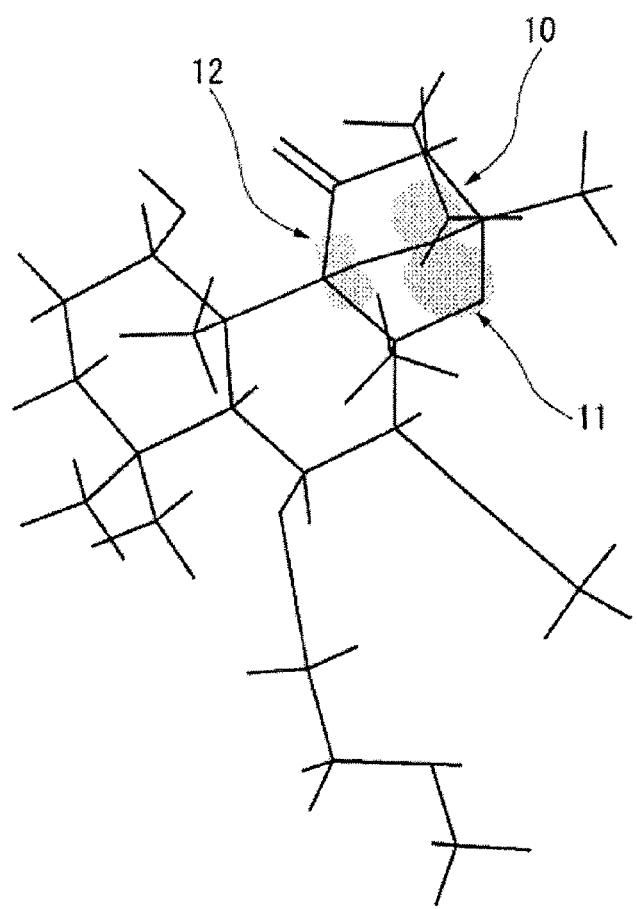
FIG. 5 is a diagram showing a three-dimensional molecular structural model of the forskolin derivative B and its spin-charge density distribution, in one embodiment of the present invention.

Similarly to the above, FIG. 5 shows a three-dimensional molecular structure of the forskolin derivative B and its spin-charge density distribution obtained by a computer simulation based on the first principle molecular dynamics method. In FIG. 5, regions 10 to 12 show upward spin-charge densities. Therefore, as shown in FIG. 4, since only upward spin states 10' to 12' are present in the forskolin derivative B, it is found to be a ferromagnetic body.

In this manner, by modifying the side chains of forskolin with specified atoms or molecules, and crosslinking between side chains present in predetermined positions, a magnetic forskolin derivative, that is, a drug, can be produced. The portion indicated with a dashed line in FIG. 2 is crosslinked. In this way, the magnitude of the magnetism of the drug can be controlled by modifying the side chains of the drug with specified atoms or molecules and/or crosslinking the side chains existing at specified positions. A user can decide as appropriate, by means of computer simulation, which functional group to insert or what form of crosslinking should be applied.

A system for realizing this computer simulation is equipped with known hardware resources for a computer: in other words, the system includes memory, an arithmetic unit with arithmetic circuits such as CPU, and display means for outputting arithmetic results. The memory stores data for specifying the three-dimensional structure of existing organic compounds and inorganic compounds and software programs for realizing the computer simulation. The software can add, change, or delete the side chains of each compound, crosslink specified side chains, calculate regions with high spin-charge densities as described above, and determine the spin-charge density of the entire structure. As such a program, for example, a commercially available product (DMOL3™ made by Accelrys K.K.) can be used.

The user inputs the position(s) to add side chains, changes the side chains, or selects the side chains to be deleted; and the user further designates the position(s) to form crosslinks to the arithmetic unit using a support program for the memory. Receiving such input values, the arithmetic unit calculates the spin-charge density and outputs the results to a display screen. Moreover, the user can find the spin-charge density of an existing compound by adding structural data of the existing compound to the computer system.

Figure 6:
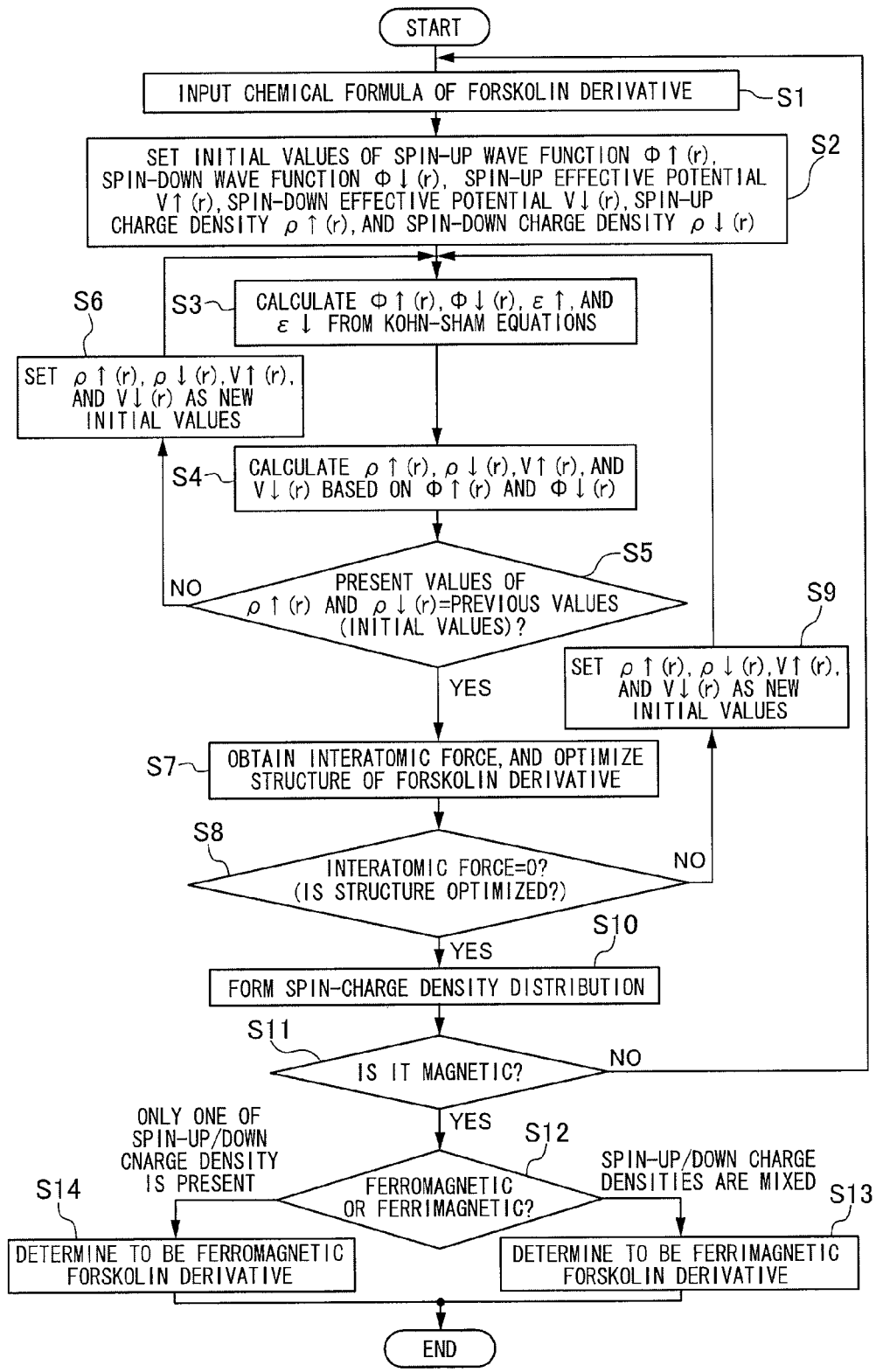
FIG. 6 is a flow chart of a drug design method in one embodiment of the present invention.

Next, a method for designing such a magnetic drug will be explained below. FIG. 6 is a flow chart showing a processing procedure of the present drug design method. The processing described hereunder is performed in a computer simulation program based on the first principle molecular dynamics method.

Firstly, since there are more than 200 types of forskolin derivatives used as drugs, a forskolin derivative serving as an evaluation target is selected from among them, and its chemical formula is input into the computer simulation program (step S1). Here, a case where the abovementioned forskolin derivative A is selected as the forskolin derivative is assumed and described hereunder. A derivative of each type of these compounds is identified by a compound library created in advance. The user inputs' the atomic number and position of each atom of each compound to the arithmetic unit.

Figure 15:
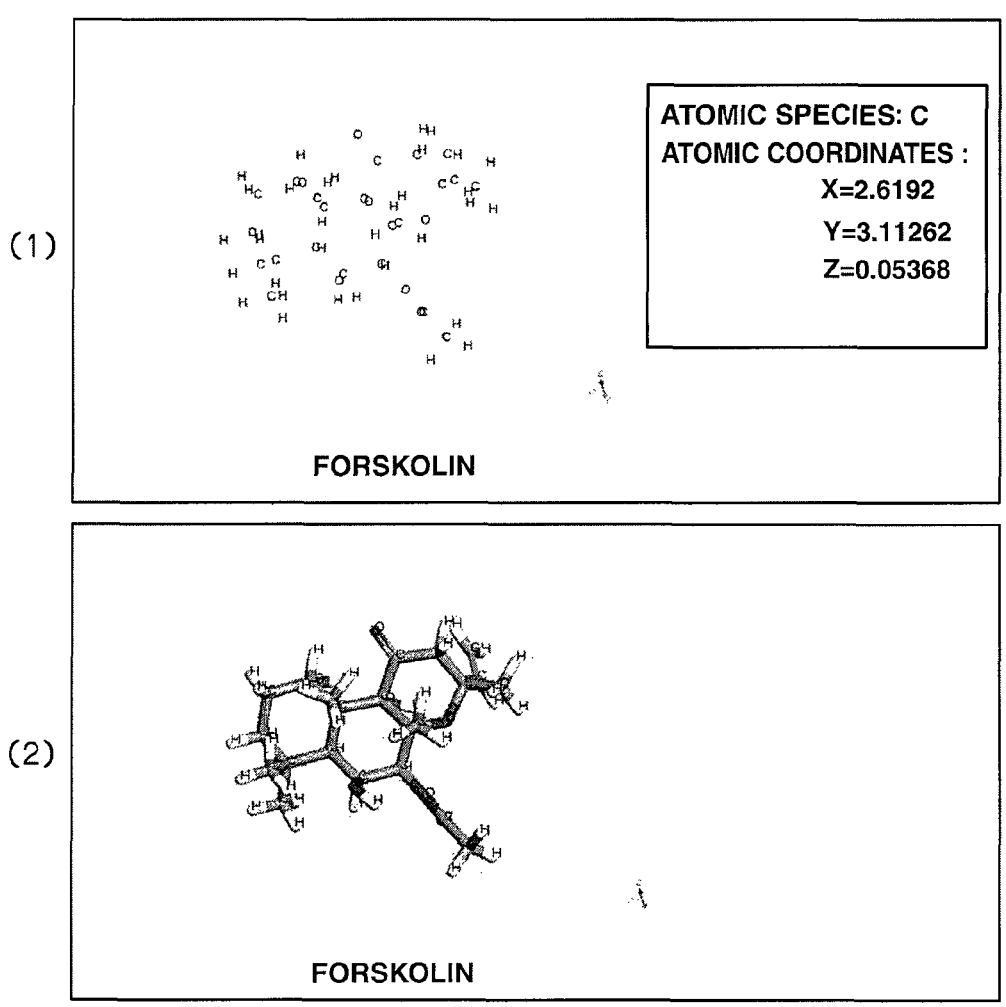
FIG. 15 is a first example of a computer output screen indicated by the computer simulation program during the process of calculating the spin-charge density of the target compound.

FIG. 15 shows screens displayed on the output device during operation in step 1. As shown in FIG. 15(1), the atomic number and atomic coordinates of one atom are input. As shown in FIG. 15(2), the bonded state of atoms such as a single bond, a double bond, or a triple bond is specified by placing a cursor at the relevant position and clicking the cursor.

The arithmetic unit receiving the above input sets, based on the above-mentioned program, initial values of upward spin (spin up) wave function $\phi\uparrow(r)$, downward spin (spin down) wave function $\phi\downarrow(r)$, spin-up effective potential $v\uparrow(r)$, spin-down effective potential $v\downarrow(r)$, spin-up charge density $\rho\uparrow(r)$, and spin-down charge density $\rho\downarrow(r)$ (step S2). Here, r is a variable showing the coordinates in the three-dimensional space.

In a case where the respective atoms constituting the forskolin derivative A are present as an isolated atom in the three-dimensional space, the spin-up wave functions $\phi\uparrow(r)$ are obtained for each of the respective atoms. The initial value of the spin-up wave function $\phi\uparrow(r)$ is the sum of all the spin-up wave functions $\phi\uparrow(r)$ that have been obtained in such a manner.

Similarly, the initial value of the spin-down wave function $\phi\downarrow(r)$ is the sum of all the spin-down wave functions $\phi\downarrow(r)$ obtained for each of the respective atoms, in a case where the respective atoms are present as an isolated atom in the three-dimensional space. Moreover, based on the spin-up wave functions $\phi\uparrow(r)$ in a case where the respective atoms constituting the forskolin derivative A are present as an isolated atom in the three-dimensional space, the spin-up effective potentials $v\uparrow(r)$ are obtained for each of the respective atoms.

The initial value of the spin-up effective potential v↑(r) is the sum of all the spin-up effective potentials v↑(r) that have been obtained for each of the respective atoms. Similarly, the initial value of the effective potential v↓(r) is the sum of all the spin-down effective potentials v↓(r) obtained for each of the respective atoms based on the spin-down wave functions φ↓(r) in a case where the respective atoms are present as an isolated atom in the three-dimensional space.

Moreover, the initial value of the spin-up charge density ρ↑(R) is obtained by substituting the spin-up wave functions φ↑(r) that have been obtained for each of the respective atoms as mentioned above, into the following operational expression (1). Moreover, the initial value of the spin-down charge density ρ↓(r) is obtained by substituting the spin-down wave functions φ↓(r) that have been obtained for each of the respective atoms, into the following operational expression (2). In the following operational expression (1), φ↑(r) is a conjugate complex number of the spin-up wave function φ↑(r). In the following operational expression (2), φ↓*(r) is a conjugate complex number of the spin-down wave function φ↓(r).

[Equation 1]

$$\rho_\uparrow(r) = \Sigma \Phi_\uparrow^*(r)\Phi_\uparrow(r) \quad (1)$$

$$\rho_\downarrow(r) = \Sigma \Phi_\downarrow^*(r)\Phi_\eta(r) \quad (1)$$

Next, based on the initial values of the spin-up effective potential v↑(r) and the spin-down effective potential v↓(r), and the initial values of the spin-up charge density ρ↑(r) and the spin-down charge density ρ↓(r), the following Kohn-Sham equations (3) and (4) are solved, so as to calculate the spin-up wave function φ↓(r), the spin-down wave function φ↓(r), the spin-up energy eigenvalue ε↑, and the spin-down energy eigenvalue ε↓, of the forskolin derivative A (step S3).

[Equation 2]

$$[-\tfrac{1}{2}\nabla^2 + V_\uparrow\{r,\rho_\uparrow(r)\}]\Phi_\uparrow(r) = \epsilon_\uparrow \Phi_\uparrow(r) \quad (3)$$

$$[-\tfrac{1}{2}\nabla^2 + V_\downarrow\{r,\rho_\downarrow(r)\}]\Phi_\downarrow(r) = \epsilon_\downarrow \Phi_\downarrow(r) \quad (3)$$

Then, based on the spin-up wave function φ↑(r) and the spin-down wave function φ↓(r) of the forskolin derivative A obtained in step S3, the spin-up charge density ρ↑(r), the spin-down charge density ρ↓(r), the spin-up effective potential v↑(r), and the spin-down effective potential v↓(r) of the forskolin derivative A are calculated (step S4). It is then determined whether or not these spin-up charge density ρ↑(r) and spin-down charge density ρ↓(r) are the same as the previous values of the spin-up charge density ρ↑(r) and the spin-down charge density ρ↓(r), which are the initial values in this case (step S5). In this step S5, if it is determined "NO", that is, the previous values (initial values) of the spin-up charge density ρ↑(r) and the spin-down charge density p↓(r) are not the same as the present values obtained in step S4, then the spin-up effective potential v↑(r), the spin-down effective potential v↓(r), the spin-up charge density ρ↑(r), and the spin-down charge density ρ↓(r) obtained in step S4 are set as new initial values (step S6). Then the flow proceeds to step S3, and the Kohn-Sham equations (3) and (4) are solved again, so as to calculate a new spin-up wave function φ↑(r), spin-down wave function φ↓(r), spin-up energy eigenvalue ε↑, and spin-down energy eigenvalue ε↓. That is, in step S5, the processing from steps S3 to S6 is repeated until the previous values of the spin-up charge density ρ↑(r) and the spin-down charge density ρ↓(r) become equal to the present values, to thereby obtain the spin-up wave function φ↑(r), the spin-down wave function φ↓(r), the spin-up energy eigenvalue ε↑, and the spin-down energy eigenvalue ε↓(r) which satisfy the Kohn-Sham equations (3) and (4).

On the other hand, in step S5, if it is determined "YES", that is, the previous values of the spin-up charge density ρ↑(r) and the spin-down charge density ρ↓(r) are the same as the present values, then as described above, an interatomic force acting between respective atoms is calculated, based on the spin-up wave function φ↑(r), the spin-down wave function φ↓(r), the spin-up energy eigenvalue ε↑, and the spin-down energy eigenvalue ε↓(r) which satisfy the Kohn-Sham equations (3) and (4), and the structure of the forskolin derivative A is optimized (step S7). That is, the spin-up wave function φ↑(r), the spin-down wave function φ↓(r), and so forth that have been obtained by repeating steps S3 to S6, are merely the optimum values in a model on a two-dimensional plane as shown in FIG. 2, and in practice it is necessary to consider the structure of the forskolin derivative A in the three-dimensional space.

Specifically, in step S7, the respective atoms constituting the forskolin derivative A are moved for a predetermined distance in an optimum direction assumed from the spin-up wave function φ↑(r), and the spin-down wave function φ↓(r), in the three-dimensional space, and an interatomic force acting between the respective atoms at this time is calculated. If the interatomic force at this time becomes 0 and the respective atoms no longer move, it can be determined that the structure of the forskolin derivative A is optimized. Therefore, the interatomic force acting between the respective atoms after the movement is calculated, and it is, determined whether or not the interatomic force becomes 0 (step S8).

In this step S8, if it is determined "NO", that is, the interatomic force is not 0 and the structure is not optimized, then the spin-up wave functions φ↑(r) and the spin-down wave functions φ↓(r) in the structures of the respective atoms after the movement are obtained. Then, the spin-up effective potential v↑(r), the spin-down effective potential v↓(r), the spin-up charge density ρ↑(r), and the spin-down charge density ρ↑(r) obtained from the spin-up wave function φ↑(r) and the spin-down wave function φ↓(r) are set as new initial values (step S9), and the processing from steps S3 to S8 is repeated. Here, the reason the flow returns to step S3 is that the spin-up wave function φ↑(r) and the spin-down wave function φ↓(r) are changed according to the structural change of the respective atoms after the movement. Moreover, the structures of the respective atoms after the movement are memorized, and when step S7 is performed again, the respective atoms are moved again for a predetermined distance from the previous structure.

When the structure of such a forskolin derivative A is optimized, then as shown in FIG. 2, the three-dimensional structure is forcibly altered so as to crosslink the oxygen atom bonded to $C_9$ and the carbon atom bonded to $C_{13}$. The atoms selected for such a crosslinking can be optionally changed.

On the other hand, in this step S8, if it is determined "YES", that is, the interatomic force acting between the respective atoms becomes 0 and the structure of the forskolin derivative A is optimized by, for example, Jahn-Teller effect, then the spin-charge density distribution as shown in FIG. 3 is obtained, based on the spin-up wave function φ↑(r) and the spin-down wave function φ↓(r) in the optimized structure (step S10).

Here, depending on the forskolin derivative selected as the evaluation target, the spin-charge density distribution such as regions 1 to 5 shown in FIG. 3 is not generated, or if the spin-charge density distribution is generated, regions having only a very small amount of spin-charge density (that is magnetic strength) are present. Such a forskolin derivative can not be determined to be magnetic. Consequently, based on the spin-charge density distribution, firstly it is determined whether or not the forskolin derivative selected as the evaluation target is magnetic (step S11).

In step S11, if it is determined "NO", that is, the forskolin derivative selected as the evaluation target is not magnetic, the flow proceeds to step S1, and another forskolin derivative is newly selected and the magnetism is evaluated again. On the other hand, in step S11, if it is determined "YES", that is, the forskolin derivative selected as the evaluation target is magnetic, then it is determined whether it is ferromagnetic or ferrimagnetic, based on the spin-charge density distribution (step S12).

As described above, since the spin-charge density distribution shows the distribution of the spin-up charge density and the spin-down charge density; if these spin-up charge density and spin-down charge density are mixed, it can be determined to be ferrimagnetic. If only one of the spin-up charge density and the spin-down charge density is present, it can be determined to be ferromagnetic.

As shown in FIG. 3, since the spin-up charge densities (regions 2 to 5) and the spin-down charge density (region 1) are mixed in the forskolin derivative A, it is determined to be a ferrimagnetic forskolin derivative (step S13). On the other hand, for example, if the selected forskolin derivative is the forskolin derivative B, as shown in FIG. 5, only the spin-up charge densities (regions 10 to 12) are present. Therefore, it is determined to be a ferromagnetic forskolin derivative (step S14). It is also possible to obtain the magnetic strength based on the spin-charge density distribution. Incidentally, in the above-mentioned examples, side chains of a compound are portions indicated with $R_6$, $R_7$, $R_{13}$ in FIG. 1 and main chains are portions excluding the above-mentioned side chain portions from the structural formula in FIG. 1.

As described above, according to the present drug design method and design system, the magnetism of a forskolin derivative having side chains modified with various atoms or molecules, and side chains optionally crosslinked can be determined. Moreover, by producing a forskolin derivative based on a molecular model determined to be magnetic, a magnetic drug can be manufactured. Therefore, it is possible to guide the drugs to the target sites in the body by use of magnetism of the drugs themselves without using supports (carriers) made from magnetic bodies as in the conventional cases. As a result, conventional problems such as difficulties in oral administration, the large size of carrier molecules in general, or technical problems in bond strength and affinity with the drug molecules can be resolved. Furthermore, it is possible to realize a drug delivery system which is easy to put into practical application.

In the above first embodiment, regarding both the forskolin derivatives A and B, the three-dimensional structure is forcibly altered so as to crosslink the oxygen atom bonded to $C_9$ and the carbon atom bonded to $C_{13}$. However, the types of atoms to be crosslinked are not limited to the above examples; and other atoms may be selected to be crosslinked. Moreover, by not performing crosslinking, but by simply changing an atom or a molecule for modifying the side chain, whether the relevant derivative is magnetic or not may be determined.

Moreover, in the above first embodiment, forskolin is used as an organic compound for description. However, the type of organic compound to be used is not limited to this, and other organic compounds may be used. Hereunder is a description of, as another organic compound, a composition effective in treatments of male erectile dysfunction, more specifically, a composition inhibiting the activity of phosphodiesterase 5 (PDE 5), which hereinafter will be referred to as "PDE 5 inhibitor". Drugs having this PDE 5 inhibitor as an active ingredient are used as remedies for male erectile dysfunction such as so-called Viagra®.

Figure 7A:
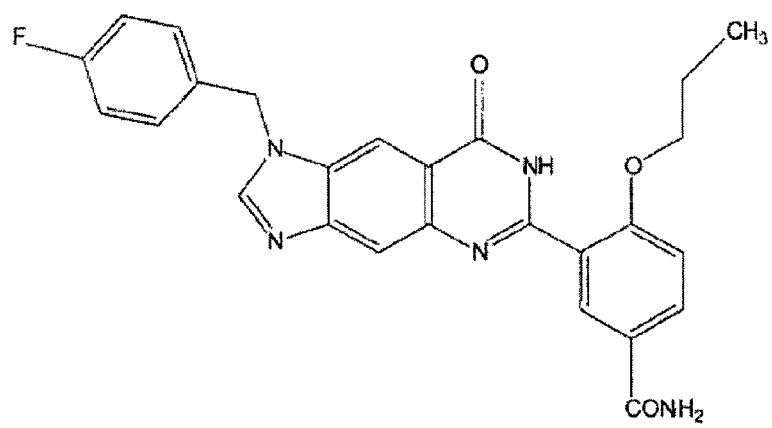
FIG. 7 shows a diagram of a basic molecular structural model of PDE 5 inhibitor with a standard composition and a three-dimensional molecular structure and spin-charge density distribution of the PDE 5 inhibitor with a standard composition in one embodiment of the present invention.
Figure 7B:
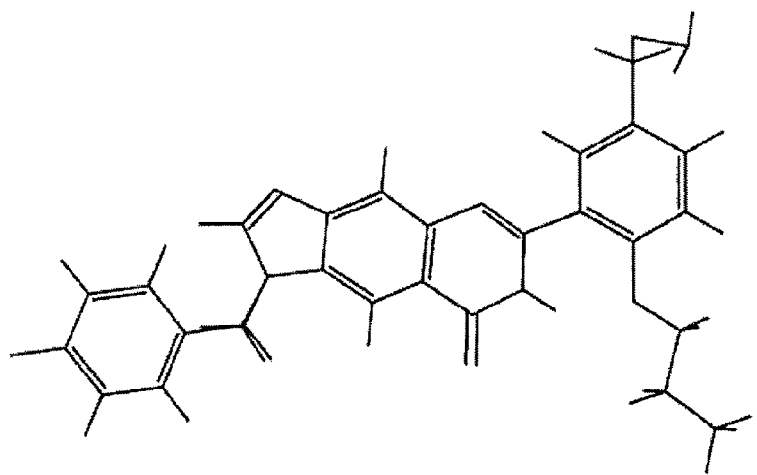
Figure 8A:
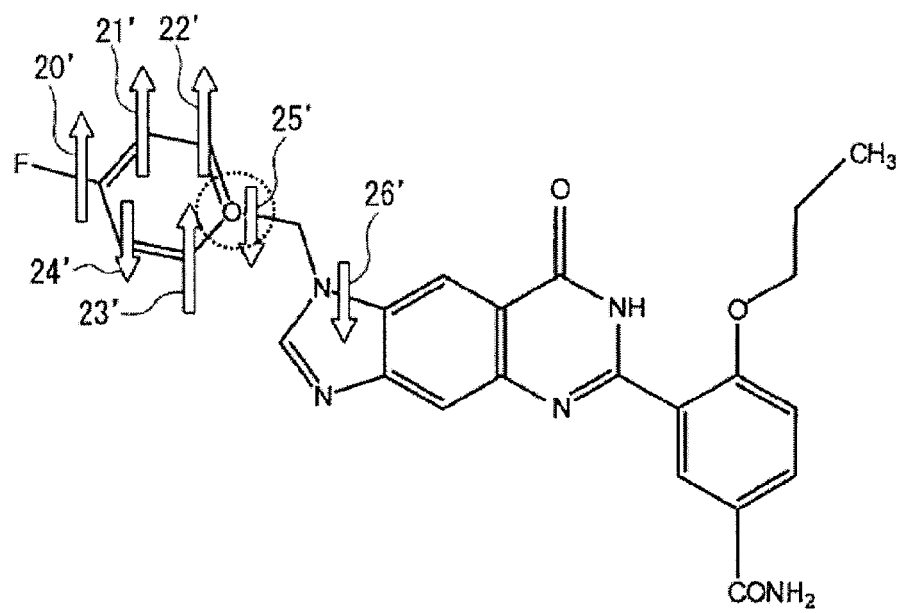
FIG. 8 shows a diagram of a basic molecular structural model of a derivative of PDE 5 inhibitor and a three-dimensional molecular structural model and spin-charge density distribution of the derivative of PDE 5 inhibitor in one embodiment of the present invention.
Figure 8B:
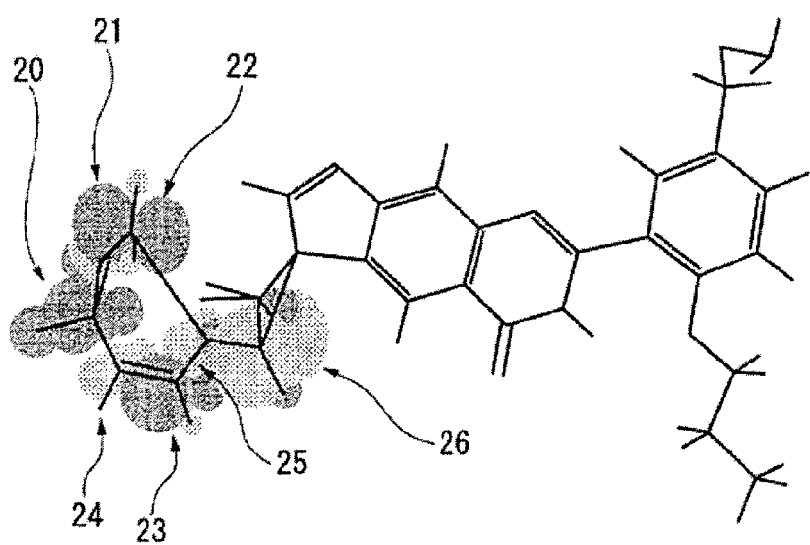

FIG. 7A is a diagram of a basic molecular structural model of PDE 5 inhibitor with a standard composition and FIG. 7B shows a three-dimensional molecular structure and spin-charge density distribution of the PDE 5 inhibitor with a standard composition that are obtained by a computer simulation in the abovementioned drug design method. On the other hand, FIG. 8A is a diagram of a basic molecular structural model of a PDE 5 inhibitor derivative derived by subjecting the PDE 5 inhibitor with a standard composition to side chain modifications. FIG. 8B shows a three-dimensional molecular structure and spin-charge density distribution of the PDE 5 inhibitor derivative obtained by the abovementioned computer simulation. In FIG. 8B, the regions 20 to 23 show upward spin-charge densities, and the regions 24 to 26 show downward spin-charge densities. Therefore, the PDE 5 inhibitor derivative is a ferrimagnetic body where the upward spin states 20' to 23' and the downward spin states 24' to 26' coexist as shown in FIG. 8A.

That is, as shown in these FIGS. 7 and 8, although the PDE 5 inhibitor with a standard composition is not magnetic, the PDE 5 inhibitor derivative which is generated by side chain modification is confirmed to be magnetic. Therefore, it has been found that as a result of using a therapeutic agent for male erectile dysfunction, which has such a magnetic PDE 5 inhibitor derivative as an active ingredient, pharmacological effects of the drug can be brought out specifically in the target site and the occurrence of side effects due to the combined use with the nitro preparations can be suppressed.

Second Embodiment

Next, a second embodiment is described using an inorganic compound, more specifically, cisplatin as an anticancer agent. Cisplatin is a metal complex (platinum complex) and classified as a platinum preparation among the anticancer agents.

Figure 9:
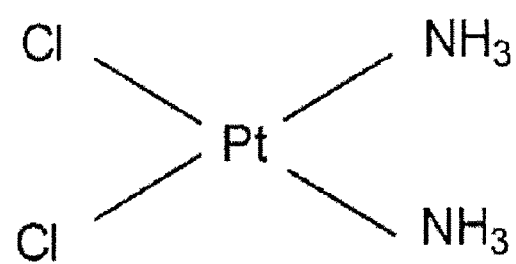
FIG. 9 is a diagram of a basic molecular structural model of cisplatin in one embodiment of the present invention.
Figure 10A:
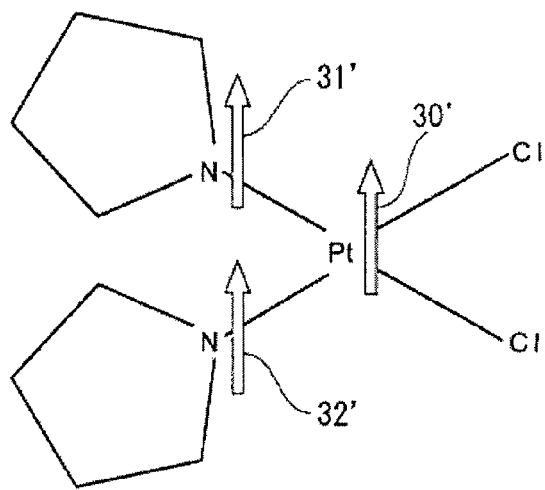
FIG. 10 shows a diagram of a basic molecular structural model of a cisplatin derivative (Cis-Pt-a3) and a three-dimensional molecular structural model and spin-charge density distribution of the cisplatin derivative (Cis-Pt-a3) in one embodiment of the present invention.

FIG. 9 is a diagram of a basic molecular structural model of cisplatin with a standard composition. Using the computer simulation by the drug design method described in the first embodiment, this cisplatin with a standard composition is confirmed to be non-magnetic. On the other hand, FIG. 10A is a diagram of a basic molecular structural model of a cisplatin derivative (Cis-Pt-a3), which is derived by subjecting the cisplatin with a standard composition to side chain modifications. Additionally, FIG. 10B shows a three-dimensional molecular structure and spin-charge density distribution of the cisplatin derivative (Cis-Pt-a3) obtained by the abovementioned computer simulation.

Figure 10B:
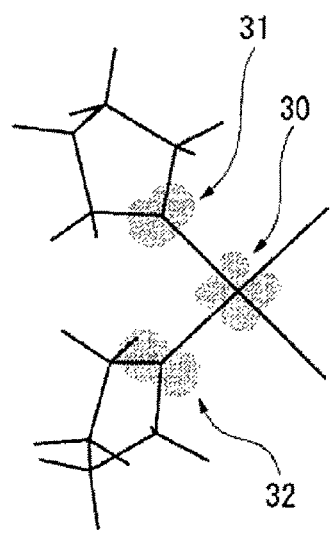

In FIG. 10B, the regions 30 to 32 show upward spin-charge densities. Therefore, the cisplatin derivative (Cis-Pt-a3) is found to be a ferromagnetic body where the upward spin states 30' to 32' exist as show in FIG. 10A. That is, using the computer simulation by the present drug design method, the cisplatin derivative (Cis-Pt-a3) is confirmed to be magnetic. Therefore, by using an anticancer agent, which has such a magnetic cisplatin derivative (Cis-Pt-a3) as an active ingredient, pharmacological effects of the drug can be brought out specifically in the cancer tissues and the occurrence of side effects can be suppressed.

The stronger the magnetism of a drug, the more efficiently the drug can be guided to the target site, and thus, a greater increase in pharmacological effects and suppression of side effects can be expected. Accordingly, the present inventors carried out an analysis of magnetic strength for various cisplatin derivatives using the computer simulation by the present drug design method. The analytical results are described below. Since the magnetic strength is in a linear relationship with the spin-charge density, the spin-charge densities in various cisplatin derivatives are analyzed in the present embodiment.

Figure 16:
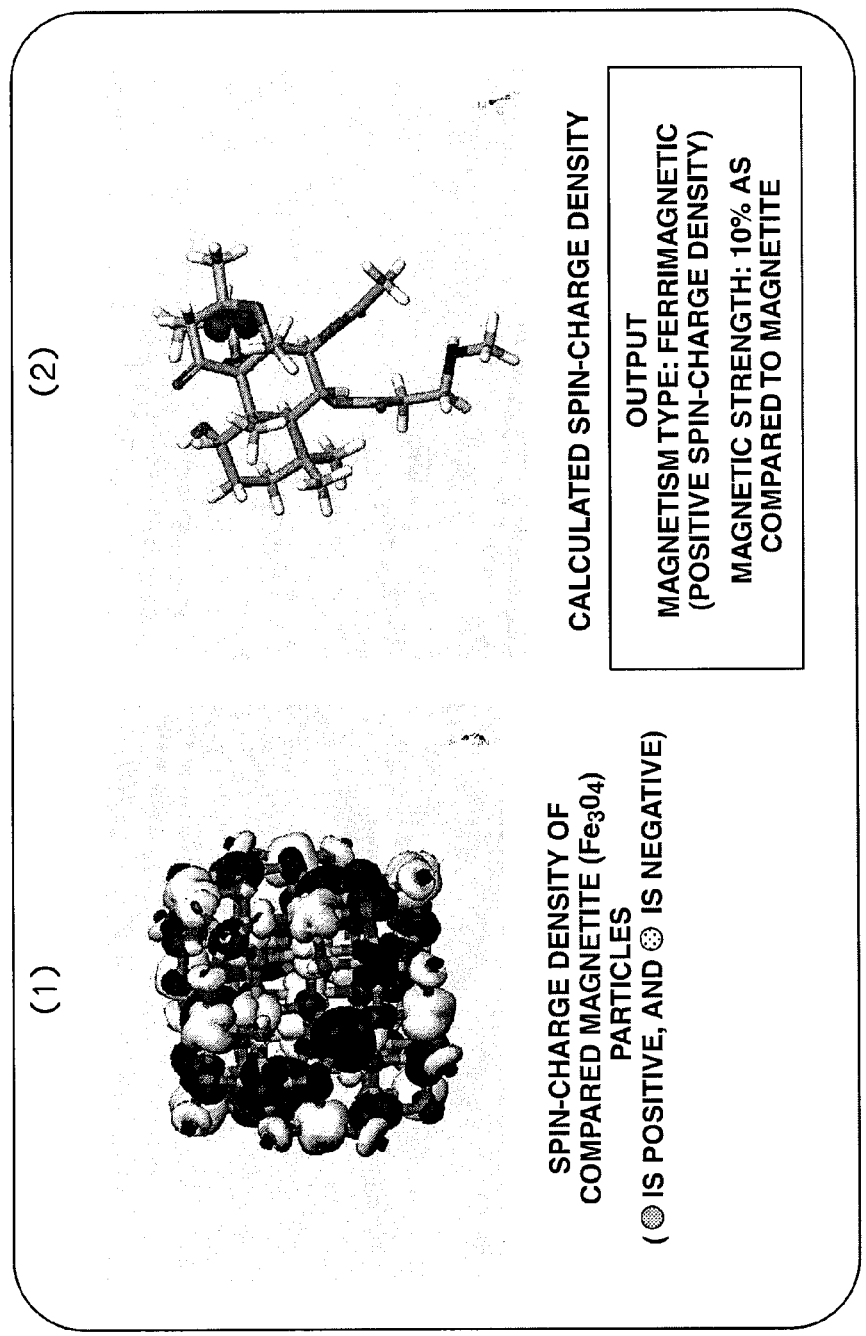
FIG. 16 is a second example of a computer output screen indicated by the computer simulation program during the process of calculating the spin-charge density of the target compound.

Firstly, as a reference, particles having a total number of 101 atoms and which were approximately 8 Å on a side were cut out from a magnetite ($Fe_3O_4$) crystal and were set as the molecular models, and after electronic states and structures were optimized by the above-mentioned computer simulation, the analysis of spin-charge densities was performed. Then, by adopting the spin-charge density of the abovementioned magnetite particles as the standard, the analysis of spin-charge densities for various cisplatin derivatives was similarly carried out. FIG. 16 shows operation screens displayed during processing corresponding to step 12 of the aforementioned computer simulation. FIG. 16(1) shows the spin-charge density of the compared magnetite. ● indicates that the spin-charge density is positive; and ○ indicates that the spin-charge density is negative. FIG. 16(2) shows the calculated spin-charge density. The type of magnetism is ferrimagnetic (positive spin-charge density) and the magnetic strength is 10% as compared to magnetite.

Furthermore, in addition to the cisplatin derivatives, various derivatives where platinum (Pt) of the cisplatin derivatives was substituted by palladium (Pd), rhodium (Rh), iridium (Ir), gold (Au), nickel (Ni), silver (Ag), copper (Cu), or cobalt (Co) were similarly analyzed for their spin-charge densities. The derivatives generated by the substitution of platinum in the cisplatin derivatives with the abovementioned metal elements, as described above, are known to have effects in inhibiting the replication of DNA which is accompanied with the propagation of cancer cells, similarly to cisplatin or cisplatin derivatives.

FIG. 11 shows the analytical results of spin-charge densities of various cisplatin derivatives and of various derivatives where platinum (Pt) of the cisplatin derivatives was substituted by palladium (Pd), rhodium (Rh), iridium (Ir), gold (Au), nickel (Ni), silver (Ag), copper (Cu), or cobalt (Co), when the spin-charge density of the magnetite particles was standardized to "1".

Figure 12:
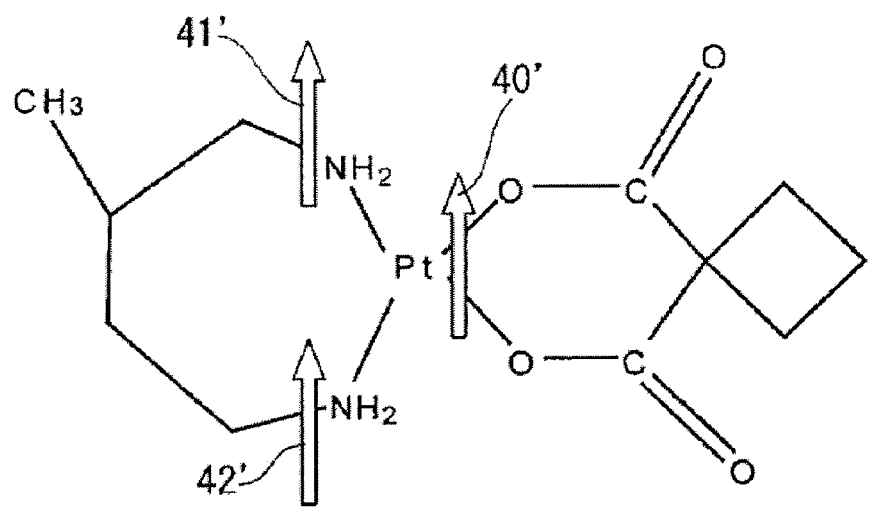
FIG. 12 is a diagram of a basic molecular structural model of the cisplatin derivative NK121, and its three-dimensional molecular structural model and spin-charge density distribution in one embodiment of the present invention.

As shown in FIG. 11, among the cisplatin derivatives, it was found that NK121 had approximately 60% of spin-charge density compared to that of the magnetite particles and is effective as a magnetic drug compared to other cisplatin derivatives. This cisplatin derivative NK121 is one which once managed to reach clinical development after a safety test. However, since the anticancer effect thereof was comparable to that of cisplatin, it was determined to have no merits surpassing cisplatin and the development thereof was suspended. Therefore, if this cisplatin derivative NK121 is taken and the guidance of the drug to the target site by means of a magnetic field is performed, drug effects would increase and side effects can also be suppressed to a large extent. FIG. 12 shows a diagram of a basic molecular structural model of the cisplatin derivative NK121. As shown in this diagram, the cisplatin derivative NK121 is a ferromagnetic body where the upward spin states 40' to 42' exist.

Moreover, the derivatives where platinum (Pt) of the cisplatin derivatives was substituted by palladium (Pd) were also confirmed to have spin-charge densities to some extent and thus, were magnetic bodies. In addition, among the derivatives where platinum (Pt) of the cisplatin derivatives was substituted by rhodium (Rh), Cis-Rh-a3 was found to have approximately 50% of spin-charge density compared to that of the magnetite particles and was effective as a magnetic drug. Further, the derivatives where platinum (Pt) of the cisplatin derivatives was substituted by iridium (Ir) were confirmed to have considerably small spin-charge densities and not many effects as magnetic drugs. Additionally, the derivatives where platinum (Pt) of the cisplatin derivatives was substituted by gold (Au) were also confirmed to have spin-charge densities to some extent and were magnetic bodies.

Moreover, the derivatives where platinum (Pt) of the cisplatin derivatives was substituted by nickel (Ni) generally had approximately 50% of spin-charge densities compared to those of the magnetite particles and were found to be effective as magnetic drugs. Additionally, the derivatives where platinum (Pt) of the cisplatin derivatives was substituted by silver (Ag) were also confirmed to have spin-charge densities to some extent and were magnetic bodies. In addition, the derivatives where platinum (Pt) of the cisplatin derivatives was substituted by copper (Cu) were also confirmed to have spin-charge densities to some extent and were magnetic bodies. Furthermore, it was found that the derivatives where platinum (Pt) of the cisplatin derivatives was substituted by cobalt (Co) had, among higher ones thereof, approximately 95% of spin-charge densities compared to those of the magnetite particles, and also, generally had considerably high spin-charge densities, and were highly effective as magnetic drugs.

As described so far, according to the drug design method in the present embodiment, not only with the drugs comprising organic compounds but also with those comprising inorganic compounds, it is possible to analyze whether they are magnetic or not from molecular models thereof. Moreover, by examining drugs with high magnetic strength (that is, with high drug effects) in advance, it will become possible to design effective drugs with a considerably high efficiency.

The above-described cisplatin derivatives and the derivatives where platinum of the cisplatin derivatives was substituted by other metal elements are cis geometric isomers. Such cis geometric isomers are used as anticancer agents since they have higher effects at inhibiting the replication of DNA which is accompanied with the propagation of cancer cells than those in trans geometric isomers. However, according to the drug design method in the present embodiment, targeted drugs can be analyzed whether they are magnetic or not, not only when they are cis geometric isomers of anticancer agents or the like, but also when they are the metal complexes composed of trans geometric isomers or when they are other inorganic compounds. Therefore, it is also possible to design magnetic drugs comprising the metal complexes composed of trans geometric isomers, or other inorganic compounds.

Next is a description of a guidance system for guiding the abovementioned magnetic drug to a target site. This guidance system may be any system as long as it generates a magnetic field, and various forms of systems can be considered. For example, application of magnetic resonance imaging (MRI) is considered, and the MRI system may be configured so that a magnetic field is irradiated to the human body and the magnetic field is controlled so as to guide the drug to the target site. Moreover, for example, a magnetic material such as a magnet may be adhered onto the skin surface of the target site. As a result, the drug that has reached the vicinity of the target site is guided to the target site, and stays specifically at the target site, causing no side effects to other normal cells. According to the above guidance system, it is possible to selectively and specifically guide a magnetic drug to the target site.

Furthermore, using the magnetism of the drugs administered in a body, it is also possible to examine the dynamics of the drugs in the body, for example, the amount of drugs accumulated in affected tissues such as cancer tissues. More specifically, using a magnetic drug as a tracer, the dynamics of the drug in the body are examined by tracing the magnetism generated from the drug with a magnetic detector. With such a magnetic detector, it is possible to examine the dynamics of drugs in the body such as the time taken for the drugs to reach the target sites after being administered in the body and thus, the present invention can not only contribute to research and development of drugs, but also determine an appropriate dose of an anticancer agent. Since there is a correlation between the accumulated amount (concentration) of a magnetic drug using the MRI and MRI images as described later, analysis of the MRI images makes it possible to find the accumulated state of a therapeutic drug in affected tissues and determine an appropriate dose.

Furthermore, functional diagnostic imaging can be performed by utilizing the magnetism and pharmacological action of the drug administered into a body. More specifically, there is a drug (such as forskolin) that has a high affinity for proteins developed in a large amount in highly malignant cancer tissues (for example, proteins called "P-glycoprotein"). The amount of forskolin accumulated in cancer tissues can be examined by making the forskolin magnetic and administering the magnetic forskolin to a cancer patient. If the accumulated amount in the cancer tissues is large, it is possible to diagnose the cancer of the patient as highly malignant; or if the accumulated amount is small, it is possible to diagnose the cancer of the patient as benign. The diagnosis of cancer malignancy grading can be made with only MRI images without taking conventional measures such as biopsy or surgery.

The same can be said for the case where affected tissues are not those of a cancer, but are those of diseases relating to receptors for neural mediators such as acetylcholine, serotonin, and dopamine in the brain. For example, the severity level of Alzheimer's dementia can be determined by examining, with MRI images of the patient's head, the dynamics of a magnetic drug which specifically binds with receptor proteins.

Figure 14:
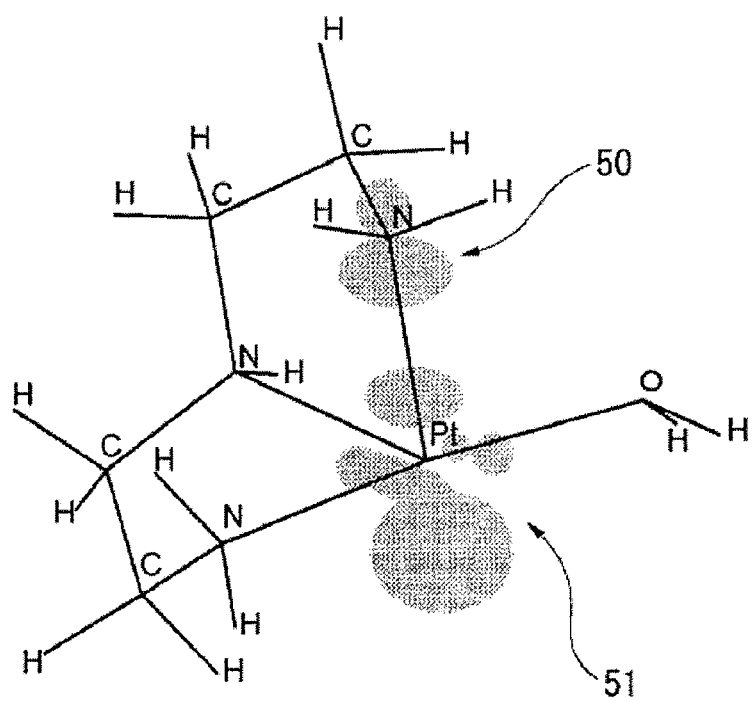
FIG. 14 is a diagram of a three-dimensional molecular structural model and spin-charge density distribution of the cisplatin hydrolysate $[Pt(OH_2)_2(dien)]^{2+}$ in one embodiment of the present invention.

It is known that when the cisplatin with a standard composition shown in FIG. 9 is administered in the body, the cisplatin is hydrolyzed by the hydrolysis process represented by the reactions 1 to 3 shown in FIG. 13, and finally generates the hydrolysis of cisplatin $[Pt(OH_2)_2(dien)]^{2+}$. As mentioned above, the cisplatin with a standard composition shown in FIG. 9 is not magnetic. However, the present inventors discovered that, based on the present drug design method, this hydrolysate of cisplatin $[Pt(OH_2)_2(dien)]^{2+}$ is magnetic. FIG. 14 shows a three-dimensional molecular structure and spin-charge density distribution of the cisplatin hydrolysate $[Pt(OH_2)_2(dien)]^{2+}$. As shown in this diagram, since the cisplatin hydrolysate $[Pt(OH_2)_2(dien)]^{2+}$ has regions 50 and 51 with upward spin-charge densities, it is found to be a ferromagnetic body.

Therefore, even with the cisplatin with a standard composition, since it is magnetic after being administered in the body, it can be guided to the target site by the abovementioned guidance system and it is also possible to examine the dynamics thereof in the body with a magnetic detector and find the amount of the drug accumulated in cancer tissues.

Figure 17:
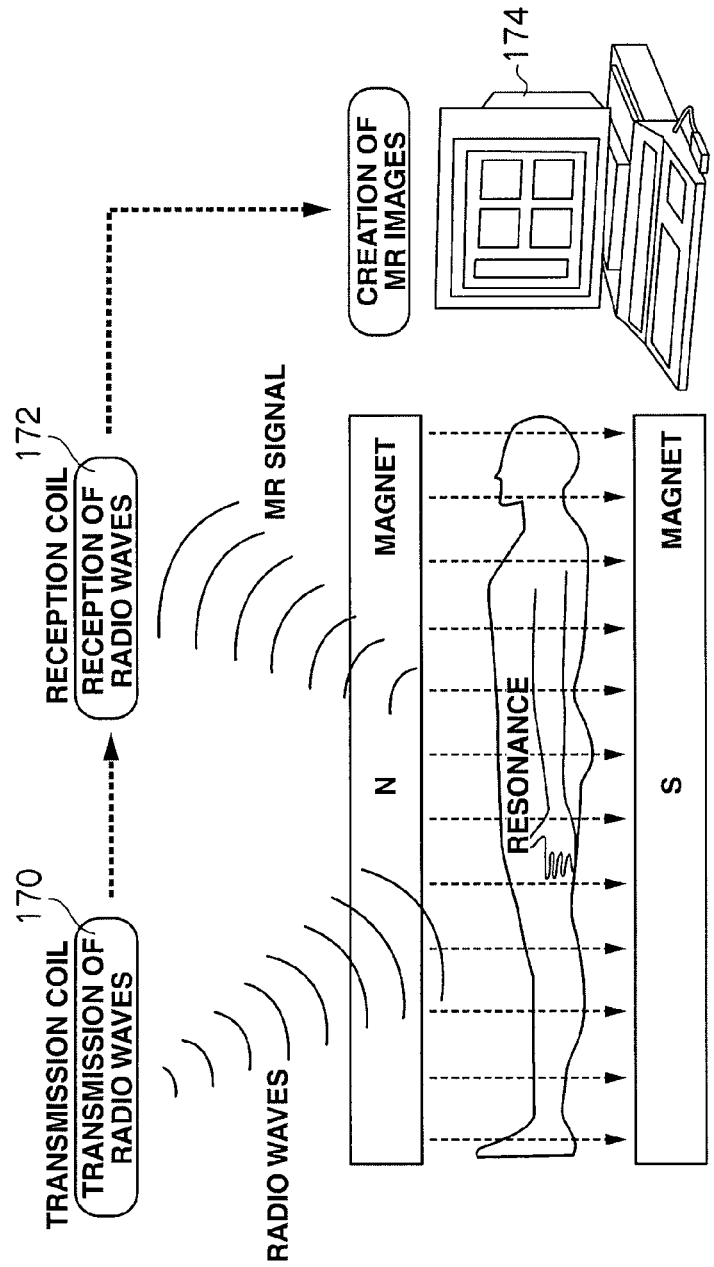
FIG. 17 is a diagram illustrating the principle of MRI.

FIG. 17 is a block diagram illustrating the principles of MRI. When the aforementioned magnetic drug is administered to a human body through, for example, oral administration, injection, or fluid administration, the human body is exposed to a magnetic field. The human body is exposed to radio waves of a specified frequency emitted from a transmission coil 170. The atomic nuclei of the administered drug molecules resonate with the radio waves and the atomic nuclei themselves then emit radio waves. A reception coil 172 receives such radio waves and synthesizes them into MR images. As a result, the location and of the drug in the human body can be visually detected.

In the tissues into which the drug has been absorbed, the atomic nuclei constituting the tissues and the atomic nuclei of the drug are in different conditions. Therefore, an MRI control unit 174 selects an appropriate frequency of radio waves to be emitted and analyzes an MR signal emitted by certain atomic nuclei. As a result, it is possible to differentiate a signal of the drug and a signal of the tissues and detect in which tissues the drug exists.

Figure 18:
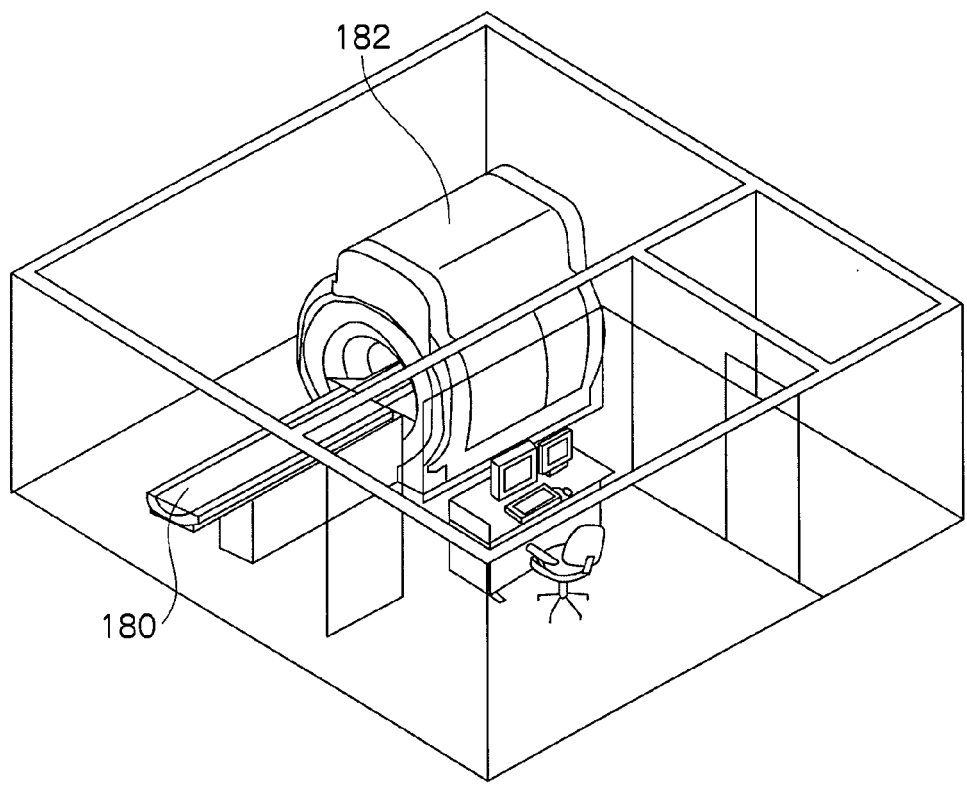
FIG. 18 is a perspective view of the entire MRI system.

FIG. 18 is a perspective view of the entire MRI system. Reference numeral 180 represents an examination table on which a test subject is placed and moved within a cylindrical magnet gantry 182. The magnet gantry is equipped with a magnet field generation device and a coil(s) for MR signal detection. The magnetic field strength of the magnet gantry is previously set to 0.2, 0.5, 1.0, or 1.5 teslas (unit). By moving the test subject within the magnetic field, the dynamics of the administered drug in the body can be controlled in accordance with the movement of the magnetic field.

Using the MRI as described above makes it possible to not only examine the dynamics of the magnetic compound in the body, but also guide the magnetic compound to a target position in the body. The magnetic compound can also be used as a contrast medium for the MRI.

Other methods besides the MRI can be adopted. A breast cancer will be explained in detail below. A breast cancer is located in breasts. If the horizontal length, the vertical length, and the depth are determined in terms of the three dimension, the site of cancer tissues of a breast cancer can be identified. The site of the breast cancer is determined in advance by, for example, the MR or CT.

Permanent magnets are tucked into an undergarment (brassiere) on the side where the cancer is located. After an anticancer agent is administered to a patient, she wears the undergarment equipped with the magnets. The anticancer agent is directly injected into the cancer tissues. For example, the anticancer agent is injected into an artery leading to the breasts or into the cancer tissues. Subsequently, the patient wears the brassiere equipped with the magnets in order to avoid diffusion of the anticancer agent from the cancer tissues to the entire body.

Moreover, the following method may also be employed. An anticancer agent is administered intravenously. The intravenously administered anticancer agent is supplied to the heart, and further passes from the aorta via the internal thoracic artery to the rami mammarii, and then finally to the breasts. The respective branches are then made subject to a magnetic field, thereby guiding the anticancer agent there. Specifically speaking, the magnetic field is applied toward the root of the internal thoracic artery where the aorta branches into the internal thoracic artery, so that the anticancer agent will be guided to flow from the aorta to the internal thoracic artery. Regarding the magnetic field strength, it was found as a result of cell culture examinations that if the distance is short, the anticancer agent can be guided at 1 tesla (the strength used by MR). Two teslas would be enough for organs close to the skin, like in the case of a breast cancer. The magnetic field strength of the MR is normally about 1.5 teslas. Regarding the measurement sensitivity, sufficient measurement sensitivity was achieved with the condition of T1 weighted images as a result of animal experiments.

Next, an example of administering a drug to an individual body and obtaining images with the MRI system will be explained. FIG. 19 shows an MRI image taken with the MRI system, wherein the MRI image of a 9-week-old female rat (ddy by Japan SIC) was taken after administration through subcutaneous injection of a solution in which a magnetic iron complex (Fe-salen) was dissolved in pyridine (concentration: 0.137 mol/litter). As compared to the MRI image before the administration of the iron complex pyridine solution, the contrast effect can be observed in gaps between the organs and along the abdominal lining in the MRI image after the administration. The region indicated with arrows shows the iron complex accumulated in gaps between small intestines. When the MRI images were taken, small magnets were pasted to the abdominal cavity of the rat. The magnet field strength was set to 1.5 teslas in the MRI analysis.

Figure 20:
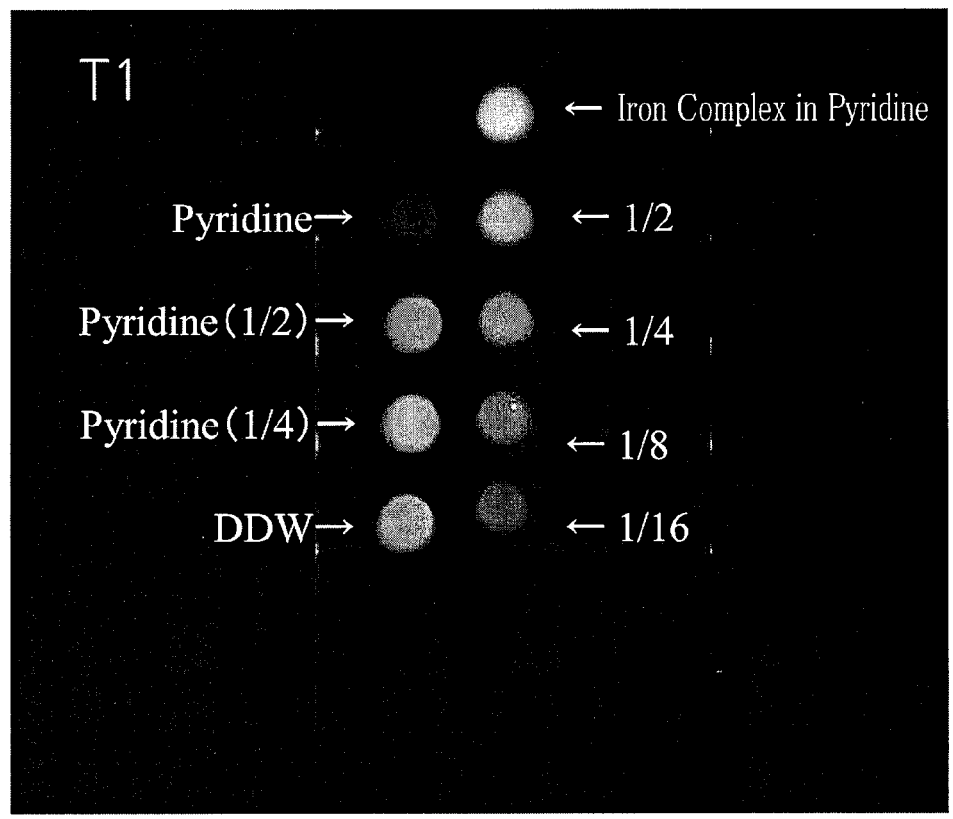
FIG. 20 is an MRI output image showing that MRI images are dependent on the concentration of a target drug.

Furthermore, FIG. 20 shows that an MRI image is dependent on the concentration of a drug. A group of samples shown on the left side is obtained by diluting a pyridine concentrate solution with water (double distilled water (DDW)), while a group of samples shown on the right side is obtained by diluting a pyridine iron complex saturated solution with pyridine. By changing the concentration of the iron complex in pyridine to, for example, ½ or ¹⁄₁₆ of the aforementioned concentration of the solution containing only pyridine, the MRI can detect changes in the concentration through images. Subsequently, when rat L6 cells were in 30% confluent state, Fe complex powder was sprinkled over a culture medium as much as required to enable visual observation of the Fe complex powder when being drawn to magnets. 48 hours later, the condition of the culture medium was photographed.

Figure 21:
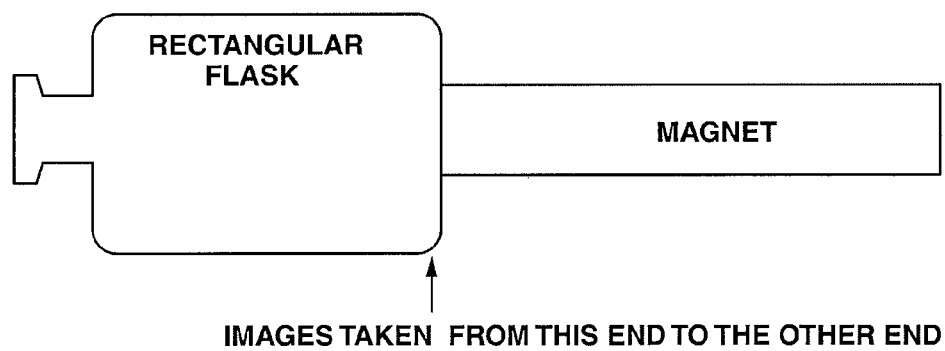
FIG. 21 is a block diagram illustrating the outline of an experiment system for verifying the location of a drug in a magnetic field.
Figure 22:
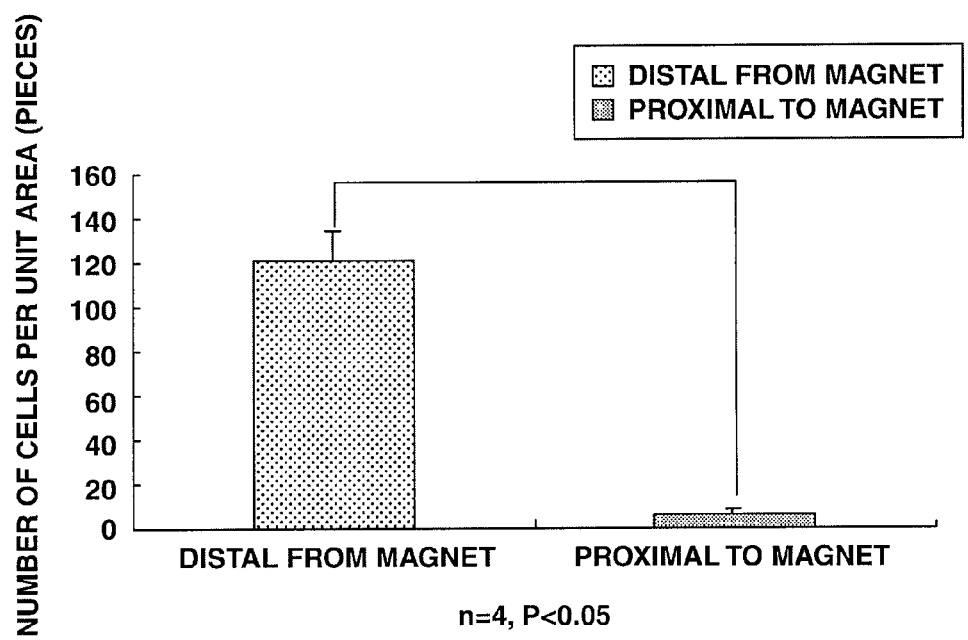
FIG. 22 is a chart showing characteristics of the measurement results of the number of cells in accordance with fluctuations in the drug concentration in a magnetic field.

FIG. 21 shows the state where a bar magnet is made to be in contact with a rectangular flask with the culture medium for the rat L6 cells. Next, FIG. 22 shows the calculation results of the number of cells by photographing the bottom face of the rectangular flask from its one end to the other end 48 hours later. Referring to FIG. 22, "proximal to magnet" means within the projected area of the bottom of the rectangular flask in contact with the end face of the magnet, while "distal from magnet" means an area of the rectangular flask opposite the end face of the magnet. FIG. 22 shows that at the area proximal to the magnet, the iron complex is drawn to the magnet and the concentration of the iron complex increases accordingly, and the number of cells is extremely low, as compared to the area distal from the magnet, because of DNA inhibition effect of the iron complex. As a result, the magnetic drug and the system including the magnetic field generating means according to the present invention can concentrate the drug at the target affected part or tissues of an individual body.

Figure 23:
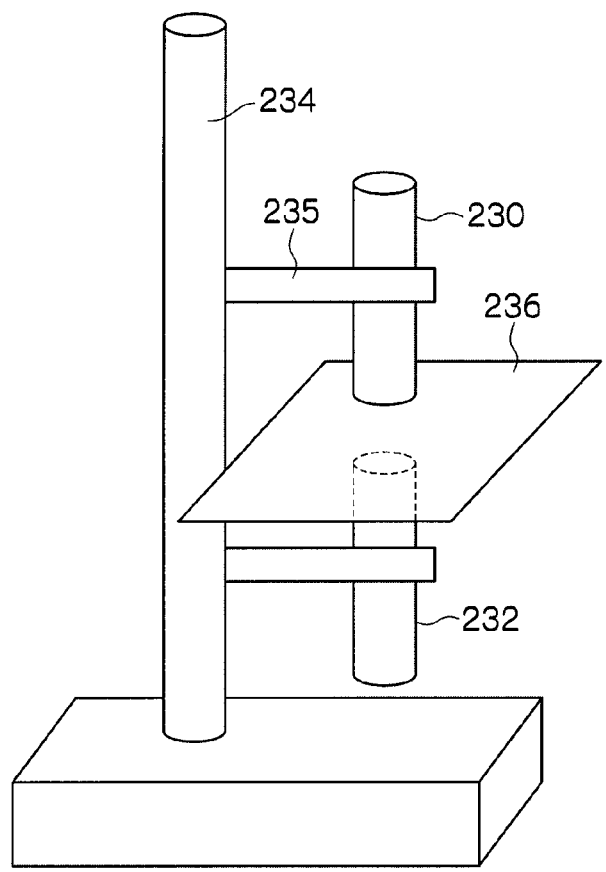
FIG. 23 is a perspective view illustrating another embodiment of a guidance system according to the present invention.

Next, another example of a guidance system according to the present invention will be explained. In this guidance system, a pair of magnets 230 and 232 located opposite to each other in a direction of gravitational force is supported by a stand 234 and a clamp 235, and a metal plate 236 is placed between the magnets as shown in FIG. 23. A locally uniform and strong magnet field can be generated by placing the metal plate, particularly an iron plate, between the pair of magnets.

In this guidance system, electromagnets can be placed instead of the above-described magnets, so that the magnetic force to be generated can be made variable. Furthermore, a pair of magnetic force generating means may be designed to be movable in X, Y, and Z directions so that the magnetic force generating means can be moved to the target position of the individual body on the table.

The drug can be concentrated on the target tissues by placing the tissues of the individual body in this area of the magnetic field. The aforementioned metal complex (drug concentration: 5 mg/ml (15 mM)) was administered intravenously to a mouse (weight: approximately 30 g), the abdominal cavity of the mouse was opened, and the mouse was then placed on the iron plate so that its right kidney was positioned between the pair of magnets.

Figure 24:
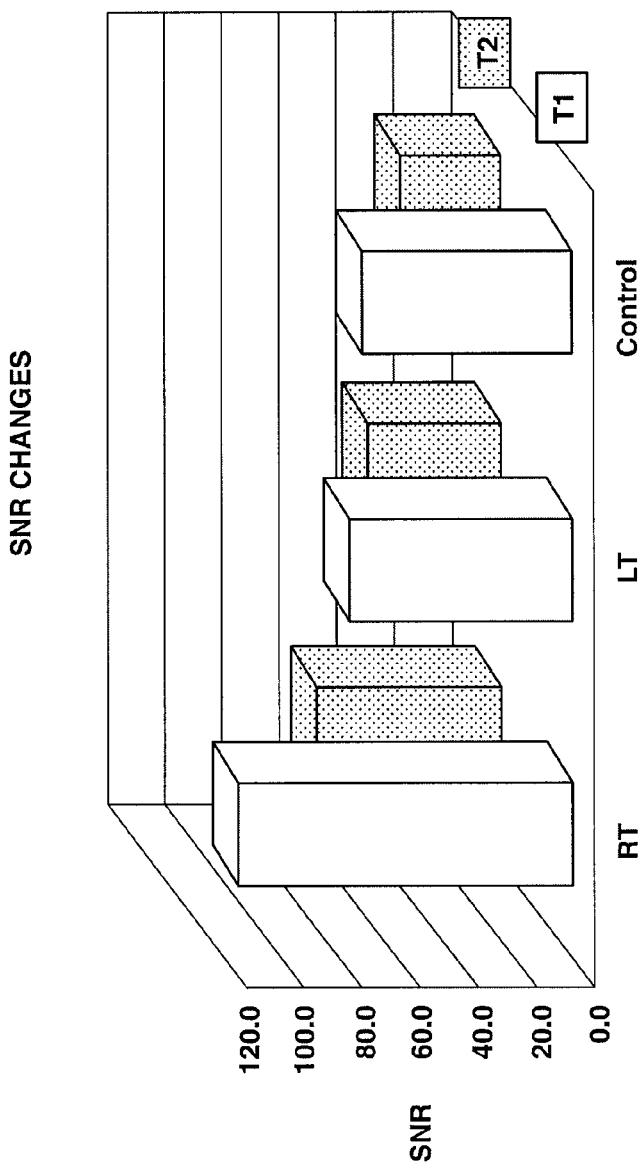
FIG. 24 is a graph showing the MRI measurement results on mouse kidneys.

The magnets used were neodymium permanent magnets made by Shin-Etsu Chemical Co., Ltd. (product number: N50; residual magnetic flux density: 1.39-1.44 T). The magnetic field then applied to the right kidney was approximately 0.3 (T) and the magnetic field applied to the left kidney was approximately ¹⁄₁₀ of that for the right kidney. The magnetic field was applied to the mouse's right kidney; and 10 minutes later, the SNR of the right kidney as well as the left kidney and another kidney (control) to which no magnetic field was applied was measured in T1 mode and T2 mode, using the MRI system. As a result, it was confirmed as shown in FIG. 24 that a larger amount of the drug could be held in the tissues of the right kidney (RT), to which the magnetic field was applied, than in the left kidney (LT) or the control.

What is claimed is:

1. A system that responds to a drug, the drug comprising an organic or inorganic compound, the drug being made magnetic by modification of side chains and/or crosslinking between side chains so that the drug can be guided to an affected part by a magnetic force applied externally.

2. A system according to claim 1, the system including a guide system for guiding the drug administered into an individual body, to a specified affected part using magnetism of the drug, wherein the guide system including means for generating a magnetic field on the surface of the individual body or at the tissues or affected part of the individual body.

3. A system according to claim 1, the system including a guide system for guiding the drug administered into an individual body to a specified affected part using the magnetism of the drug, the guide system comprising:
   means for generating a magnetic field to the individual body; and
   means for guiding the magnetic field to target tissues or affected part of the individual body.

4. A system according to claim 2, the system comprising magnetic field generating means comprising two magnets, forming a pair, and positioned so that the target tissues or affected part is positioned between the two magnets to focus a magnetic flux on the tissues or affected part.

5. A system according to claim 2, wherein the target tissues or affected part is identified in an MRI or CT system.

6. A system according to claim 1, the system including a magnetic detection system, wherein by detecting the magnetism of the drug administered in a body, the dynamics of the drug in a body are detected.

7. The system according to claim 6, wherein the magnetism is detected by magnetic resonance guidance.

8. A system according to claim 3, the system comprising magnetic field generating means comprising two magnets, forming a pair, and positioned so that the target tissues or affected part is positioned between the two magnets to focus a magnetic flux on the tissues or affected part.

9. A system according to claim 3, wherein the target tissues or affected part is identified in an MRI or CT system.

10. A system according to claim 4, wherein the target tissues or affected part is identified in an MRI or CT system.

11. A drug having side chains providing positive or negative spin-charge density bound to a basic skeleton of an organic compound, and having a degree of magnetism sufficient to enable the drug to be guided as a whole by magnetic resonance to an outside magnetic field so that when the drug is applied to a human or animal body, the drug is guided to and retained in a target area to which a magnetic field is locally generated by the magnetic field outside the body, and exhibits the medical effect of the drug in the target area.

12. A magnetic drug guidance system for controlling a position of an applied magnetic field so as to guide a magnetic drug, by the applied magnetic field from outside the body, to an affected part of the body in which the magnetic drug exerts an effect after the magnetic drug has been administered into the body, the magnetic drug comprising an organic or inorganic compound made magnetic by modification of side chains and/or crosslinking between side chains, the magnetic drug guidance system comprising:
  a first mechanism configured to detect the affected part of the body;
  a second mechanism configured to generate, from outside the body, a magnetic force acting on the magnetic drug, the second mechanism providing the body with the magnetic force; and
  a third mechanism configured to move the second mechanism to a position in which the magnetic drug administered systemically is guided to a target site of the affected part,
  wherein the third mechanism enables accumulation of the magnetic drug in the target site of the affected part by moving the second mechanism so that the magnetic drug is guided to the target site of the affected part.

13. The magnetic drug guidance system according to claim 12, further comprising:
  a fourth mechanism configured to obtain an image of the magnetic drug in the body using the magnetic drug as a contrast medium; and
  a fifth mechanism configured to obtain dynamics of the magnetic drug in the body based on the image obtained by the fourth mechanism,
  wherein the third mechanism moves the second mechanism based on the dynamics obtained by the fifth mechanism.

14. The magnetic drug guidance system according to claim 13,
  wherein the fourth mechanism obtains an image dependent on a concentration of the magnetic drug,
  the magnetic drug guidance system further comprising:
  a sixth mechanism configured to detect an amount of the magnetic drug accumulated in the target site of the affected part based on the image obtained by the fourth mechanism; and
  a seventh mechanism having magnetic strength sufficient to concentrate and to retain in the affected part the magnetic drug accumulated in the target site of the affected part, the seventh mechanism comprising a magnet for applying the magnetic strength to the affected part from outside the body.

15. The magnetic drug guidance system according to claim 12, wherein the magnetic drug has magnetism sufficient to enable the magnetic drug to be guided to the target site of the affected part by the applied magnetic field from outside the body without using a support,
  wherein the third mechanism guides the magnetic drug to the affected part using the magnetism of the magnetic drug, and the second mechanism applies the magnetic force to the magnetic drug.

16. The magnetic drug guidance system according to claim 15, wherein the magnetic drug is a salen complex compound.

17. The magnetic drug guidance system according to claim 12, wherein the magnetic drug is administered intravenously or orally.

18. A detection system for detecting the dynamics of a magnetic drug in a body, the magnetic drug comprising an organic or inorganic compound which is made magnetic by modification of side chains and/or crosslinking between side chains, the detection system comprising:
  a first mechanism configured to generate a magnetic field;
  a second mechanism configured to differentiate tissue of an affected part and the magnetic drug in the body based on the magnetic field generated by the first mechanism, the second mechanism obtaining an image dependent on a concentration of the magnetic drug based on magnetism of the magnetic drug; and
  a third mechanism configured to enable analysis of an amount of the magnetic drug accumulated in the tissue of the affected part based on the image obtained by the second mechanism,
  wherein the magnetic drug has magnetism sufficient to enable the magnetic drug to be guided to the tissue of the affected part without using a support, the magnetic drug having an affinity for tissue of the affected part,
  wherein the second mechanism obtains an image exhibiting presence of the magnetic drug in the tissue of the affected part by differentiating the tissue of the affected part and the magnetic drug in the body based on the magnetic field generated by the first mechanism.

19. The detection system according to claim 18, wherein the second mechanism obtains the image of the tissue of the affected part by differentiating the magnetic drug that specifically binds with a protein in the tissue of the affected part, from the tissue of the affected part.

20. The detection system according to claim 18, wherein the tissue of the affected part is a malignant tumor or a receptor for a neural mediator.

21. A self-magnetic compound comprising an organic or inorganic compound, the compound being made magnetic by modification of side chains and/or crosslinking between side chains so that when the compound is applied to a human or animal body, a magnetism of the compound is sufficient to make the compound magnetically detectable.

22. The compound according to claim 21, wherein the compound is a metal complex.

23. The compound according to claim 22, wherein the metal complex is a metal-salen complex.

24. The compound according to claim 22, wherein the metal-salen complex is an iron-salen complex.

25. The compound according to claim 22, wherein the metal-salen complex is an iron-salen complex.

26. The compound according to claim 21, wherein the compound is detectable by magnetic resonance imaging.

27. The compound according to claim 26, wherein the compound is suitable for use as a contrast medium for magnetic resonance imaging.

28. A self-magnetic compound suitable for use as a magnetically detectable compound, wherein the compound comprises a metal-salen complex.

29. The compound according to claim 28, wherein the metal-salen complex is a iron-salen complex.

30. The compound according to claim 28, wherein the compound is detectable by magnetic resonance imaging.

31. The compound according to claim 30, wherein the compound is suitable for use as a contrast medium for magnetic resonance imaging.

* * * * *